US007795385B2

(12) United States Patent
Schwartsmann et al.

(10) Patent No.: US 7,795,385 B2
(45) Date of Patent: Sep. 14, 2010

(54) USE OF BOMBESIN/GASTRIN-RELEASING PEPTIDE ANTAGONISTS FOR THE TREATMENT OF INFLAMMATORY CONDITIONS, ACUTE LUNG INJURY AND BIPOLAR DISORDER

(75) Inventors: Gilberto Schwartsmann, Porto Alegre (BR); Rafael Roesler, Porto Alegre (BR); Felipe Dal Pizzol, Criciuma (BR); Joao Luciano Quevedo, Criciuma (BR); Flavio Kapczinski, Porto Alegre (BR)

(73) Assignee: Bexar Global, Inc., Road Town, Tortola (VG)

( * ) Notice: Subject to any disclaimer, the term of this patent is extended or adjusted under 35 U.S.C. 154(b) by 0 days.

(21) Appl. No.: 11/299,849

(22) Filed: Dec. 13, 2005

(65) Prior Publication Data

US 2006/0160744 A1 Jul. 20, 2006

Related U.S. Application Data

(60) Provisional application No. 60/636,525, filed on Dec. 17, 2004, provisional application No. 60/748,178, filed on Dec. 8, 2005.

(51) Int. Cl.
*A61K 38/00* (2006.01)
(52) U.S. Cl. ..................................................... 530/309
(58) Field of Classification Search ........................ None
See application file for complete search history.

(56) References Cited

U.S. PATENT DOCUMENTS

| 5,244,883 A | | 9/1993 | Cai et al. | |
| 5,369,094 A | * | 11/1994 | Schally et al. | 514/15 |
| 5,747,506 A | * | 5/1998 | Naef | 514/307 |
| 2004/0110768 A1 | * | 6/2004 | Higginbottom et al. | 514/256 |

FOREIGN PATENT DOCUMENTS

| CA | 2 097 192 | | 6/1992 |
| WO | WO 92/07830 | * | 4/1992 |
| WO | WO 92/09626 | | 6/1992 |

OTHER PUBLICATIONS

Meller et al. "The bombesin/ gastrin releasing peptide receptor antagonist RC-3095 blocks apomorphine but not MK-801-induced stereotypy in mice." Peptides 2004, 25, 585-588.*
Kiaris et al. "Inhibition of gorwth of human malignant glioblastoma in nude mice by antagonists of bombesin/gastrin-releasing peptide." Oncogene, 1999, 18, 7168-7173.*
Spragg "Acute lung injury 2003." Acta Pharmacol. Sin. 2003, 24, 1288-1291.*
Machado-Vieira et al. "Perspectives for the development of animal models of bipolar disorder." Prog. Neuro-Psychopharm. & Biol. Pharm., 2004, 28, 209-224.*
LeBan et al. "Development of potent gastrin-releasing peptide antagonists having a D-Pro-psi(CH2NH)-Phe-NH2 C terminus." Proc. Natl. Acad. Sci. USA, 1993, 90, 1922-1926.*
Lorenz & Kalden, "Perspectives for TNF-alpha-targeting therapies." Arthritis Res., 2002, 4, S17-24.*
Keating & Perry, "Infliximab: an updated review of its use in Crohn's disease and rheumatoid arthritis." BioDrugs, 2002, 16, 111-48, abstract.*
Su et al., "Efficacy of anti-tumor necrosis factor therapy in patients with ulcerative colitis." Am J Gastroenterol. 2002, 10, 2577-84.*
Mease, "TNFalpha therapy in psoriatic arthritis and psoriasis." Ann Rheum Dis., 2004, 63, 755-8.*
http://www.chemexper.com/index.shtml?main=http://www.chemexper.com/search/cas/34592-47-7.html.*
"Bipolar Disorder," NIH Publication No. 02-3679, Printed 2001, Reprinted 2002 (Applicant's IDS).*
Hanns-Martin Lorenz et al "Perspectives for TNF-alpha-targeting therapies," Arthritis Research (2002) vol. 4 Suppl 3, S17-S24.*
Zamir et al, Effect of sepsis or cytokine administration on release of gut peptides, The American Journal of Surgery (1992), vol. 63, pp. 181-184.*
Benicio Noronha Frey, et al., "Increased oxidative stress in an animal model of acute mania", 2005, pp. 1-22.
Amit Anand, M.D., et al. "Brain SPECT Imaging of Amphetamine-Induced Dopamine Release in Euthymic Bipolar Disorder Patients," Am J. Psychiatry, 157:7, Jul. 2000.
David H. Coy, et al., "Probing Peptide Backbone Function in Bombesin," The Journal of Biological Chemistry, vol. 263, No. 11, Issue of Apr. 15, 1988, pp. 5056-5060.
Felipe Dal-Pizzol, et al., "Gastrin-Releasing Peptide Receptor Antagonist Effects on an Animal Model of Sepsis," Am J. Respir Crit Care Med, vol. 173, pp. 84-90, 2006.
M. De La Fuente, et al., Modulation of Phagocytic Function in Murine Peritoneal Macrophages by Bombesin, Gastrin-Releasing Peptide and Neuromedin C, Immunology, 1991, 73, pp. 205-211.
M. De L Fuente, et al., "Effect of Aging on the Modulation of Macrophage Functions by Neuropeptides," Life Sciences, 67 (2000) 2125-2135.

(Continued)

*Primary Examiner*—Cecilia Tsang
*Assistant Examiner*—Thomas S Heard
(74) *Attorney, Agent, or Firm*—Luce Forward, Technology Law Group; Marian D. Walker; Peter Jon Gluck

(57) ABSTRACT

The invention concerns the use of a bombesin/gastrin releasing peptide antagonist in the treatment of inflammatory and immune-mediated inflammatory conditions, in particular sepsis, acute lung injury and rheumatoid arthritis as well as for the treatment or prophylaxis of brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder. In particular, specific nonapeptides with antagonist properties against bombesin or bombesin-like peptides, such as the gastrin releasing peptide, may be used in the treatment of inflammatory and immune-mediated inflammatory conditions as well as brain disorders.

2 Claims, 8 Drawing Sheets

OTHER PUBLICATIONS

Monica Del Rio et al., "Chemoattractant Capacity of Bombesin, Gastrin-Releasing Peptide and Neuromedin C is Mediated Through PKC Activation in Murine Peritoneal Leukocytes," Regulatory Peptides, 49 (1994) 185-193.

Editorials, "Bombesin-Like Peptides," Am J. Respir Crit Care Med, vol. 173, pp. 1-6, 2006.

Joseph C. Fantone, M.D., "Role of Oxygen-Derived Free Radicals and Metabolites in Leukocyte-Dependent Inflammatory Reactions," AJP, vol. 107, No. 3, Jun. 1982.

Gilberto Friedman, et al., "Has the Mortality of Septic Shock Changed with Time?" Crit Care Med, 1998, vol. 26, No. 12, 2078-2086.

Laurence Genton, M.D., et al., "Interations Between the Enteric Nervous System and the Immune System: Role of Neuropeptides and Nutrition," The American Journal of Surgery, 186 (2003), pp. 253-258.

Yan-Shi Guo et al., "Activator Protein-1 Transcription Factor Mediates Bombesin-Stimulated Cyclooxygenease-2 Expression in Intestinal Epithelial Cells," The Journal of Biological Chemistry, vol. 276, No. 25, Issue of Jun. 22, 2001, pp. 22941-22947.

David C. Heimbrook, et al. "Carboxyl-Terminal Modifcation of a Gastric Releasing Peptide Derivative Generates Protein Antagonists," The Journal of Biological Chemistry, vol. 264, No. 19, Issue of Jun. 5, 1989, pp. 11258-11262.

Mark R. Hellmich, et al., "Multiple Protein Kinase Pathways Are Involved in Gastrin-Releasing Peptide Receptor-Regulated Secretion," The Journal of Biological Chemistry, vol. 274, No. 34, Issue of Aug. 20, 1999, pp. 23901-23909.

Richard S. Hotchkiss, M.D., et al., "The Pathophysiology and Treatment of Sepsis," N. Engl J. Med, 348:2, Jan. 9, 2003, pp. 138-150.

Yumiko Ishikawa-Brush, et al. "Autism and Multiple Exostoses Associated with an X;8 Translocatio Occurring Within the GRPR Gene and 3' to the SDC2 Gene," Human Molecular Genetics, 1997, vol. 6, No. 8, 1241-1250.

I. Lemaire, et al., "Bombesin-Like Peptides in Alveolar Macrophage: Increased Release in Pulmonary Inflammation and Fibrosis," Neuropeptides (1991), 20, pp. 63-72.

I. Lemaire, "Bombesin-Related Peptides Modulate Interleukin-1 Production by Alveolar Macrophages," Neuropeptides (1991), 20, 217-223.

Rodrigo Machado-Vieira, et al., "Perspectives for the Development of Animal Models of Bipolar Disorder," Progress in Neuro-Psychopharmacology & Biological Psychiary, 28, (2004) 209-224.

Husseini K. Manji, et al., "Signaling: Cellular Insights into the Pathophysiology of Bipolar Disorder," Biol Psychiatry, 2000; 48: 518-530.

H.K. Manji, et al., "PKC, MAP Kinases and the bcl-2 Family of Proteins as Long-Term Targets for Mood Stabilizers," Molecular Psychiatry, (2002) 7, S46-S56.

Sonia Medina, et al., "Changes with Ageing. in the Modulation of Murine Lymphocyte Chemotaxis by CCK-8S, GRP and NPY," Mechanisms of Ageing and Development, 102 (1998) 249-261.

S. Medina et al., "Changes with Age in the Modulation fo Natural Killer Activity of Murine Leukocytes by Gastrin-Releasing Peptide, Neuropeptide Y and Sulfated Cholecystokinin Octapeptide," Neuropeptides (1998) 32 (6), 549-555.

S. Medina et al., "Age-Related Changes in the Modulatory Action of Gastrin-Releasing Peptide, Neuropeptide Y and Sulfated Cholecystokinin Octapeptide in the Proliferation of Murine Lymphocytes," Neuropeptides (1999) 33 (2), 173-179.

Carolina A. Meller, et al., "The Bombesin/Gastrin Releasing Peptide Receptor Antagonist RC-3095 Blocks Apomorphine But No MK-801-Induced Stereotypy in Mice," Peptides, 25 (2004) 585-588.

F. Meloni et al., "Bombesin/Gastrin Releasing Peptide Levels of Peripheral Monocolear Cells, Monocytes and Alveolar Macrophagese in Chronic Bronchitis," Int. J. Tiss. Reac. XIV(4), 195-201 (1992).

Terry W. Moody et al., "Bombesin-Like Peptides and Associated Receptors Within the Brain: Distribution and Behavioral Implications," Peptides 25 (2004) 511-520.

"Bipolar Disorder," NIH Publication No. 02-3679, Printed 2001, Reprinted 2002.

Platon Peristeris, et al., "N-Acetylcysteine and Gluthatione as Inhibitors of Tumor Necrosis Factor Production," Cellular Immunology, 140, 390-399 (1992).

Kees H. Polderman, et al., "Drug Intervention Trials in Sepsis: Divergent Results," Lancet 2004, 363, 1721-23.

Sinisa Radulovic et al., Biological Effects and Receptor Binding Affinities of New Pseudononapeptide Bombesin/GRP Receptor Antagonists with N-Terminal D-Trp or D-TPI, Int. J. Peptide Protein Res. 38, 1991, 593-600.

Cristiane Ritter, et al., "Oxidative Parameters and Mortality in Sepsis Induced by Cecal Ligation and Perforation," Intensive Care Med (2003), 29: 1782-1789.

Cristiane Ritter, M.D., et al., "Treatment with N-Acetylcysteine Plus Deferoxamine Protects Rats Against Oxidative Stress and Improves Survival in Sepsis," Crit Care Med, 2004, vol. 32, No. 2.

Correspondence, www.thelancet.com, vol. 364, Aug. 7, 2004.

Rafael Roesler, et al., "Bombesin/Gastrin-Releasing Peptide Receptors in the Basolateral Amygdala Regulate Memory Consolidation," European Journal of Neuroscience, vol. 19, pp. 1041-1045, 2004.

Rafael Roesler, et al., "Neuropeptides and Anxiety Disorders: Bombesin Receptors as Novel Therapeutic Targets," Trends in Pharmacological Sciences, vol. 25, No. 5, May 2004.

Daniela Salvemini, et al., "Protective Effects of a Suerpoxide Dismutase Mimetic and Peroxynitrite Decomposition Catalysts in Endotoxin-Induced Intestinal Damage," British Journal of Pharmacology, (1999), 127, 685-692.

Kenneth E. Sands, et al., "Epidemology of Sepsis Syndrome in 8 Academic Medical Centers," JAMA, Jul. 16, 1997, vol. 278, No. 3.

G. Schwartsmann, "Dexamethasone and Gastrin-Releasing Peptide. Receptors in Human Lung Cells," Lung Cancer (2004), 46, 129, Mar. 8, 2004.

Gleb P. Shumyatsky et al., "Identification of a Signaling Network in Lateral Nucleus of Amygdala Important for Inhibiting Memory Specifically Related to Learn Fear," Cell, vol. 111, 905-918, Dec. 13, 2002.

Stephen M. Strakowski et al., "Progressive Behavioral Response to Repeated d-Amphetamine Challenge: Further Evidence for Sensitization in Humans," Biol. Psychiatry, 1998; 44: 1171-1177.

Meera Subramaniam, et al., "Bombesin-Like Peptides and Mast Cell Responses," American Journal of Respiratory and Critical Care Medicine, vol. 168, 2003, 601-611.

Csaba Szabo et al., "Role of Poly(ADP-Ribose) Synthetase in Inflammation and Ischaemia-Reperfusion," TiPS, Jul. 1998 (vol. 19), 287-298.

Karoly Szepeshazi, et al., "A Single In Vivo Administration of Bombesin Antagonist RC-3095 Reduces the Levels and mRNA Expression of Epidermal Growth Factor Receptrs in MXT Mouse Mammary Cancers," Proc. Natl. Acad. Sci., vol. 94, pp. 10913-10918, Sep. 1997.

K. Yamada et al., "Role of Bombesin (BN)-Like Peptides/Receptors in Emotional Behavior by Comparison of Three Strains of BN-Like Peptide Receptor Knockout Mice," Molecular Psychiatry (2002) 7, 113-17.

* cited by examiner

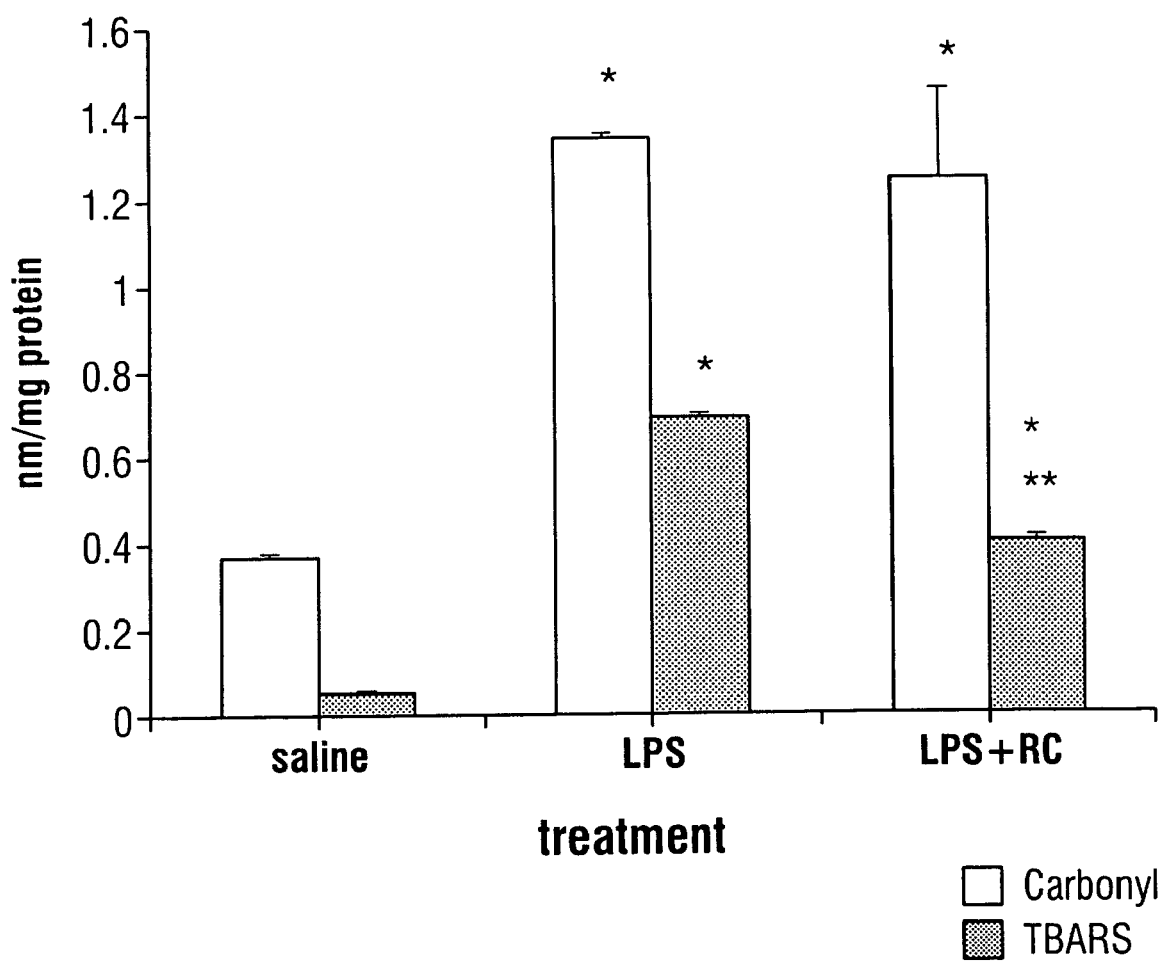

Fig. 6
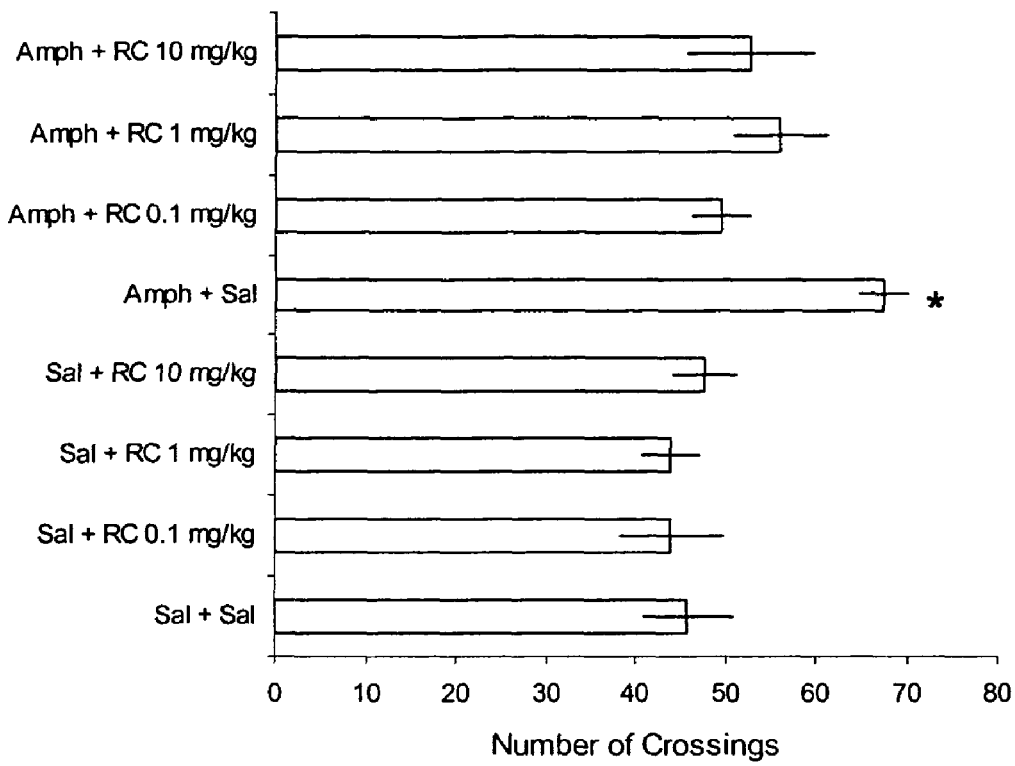
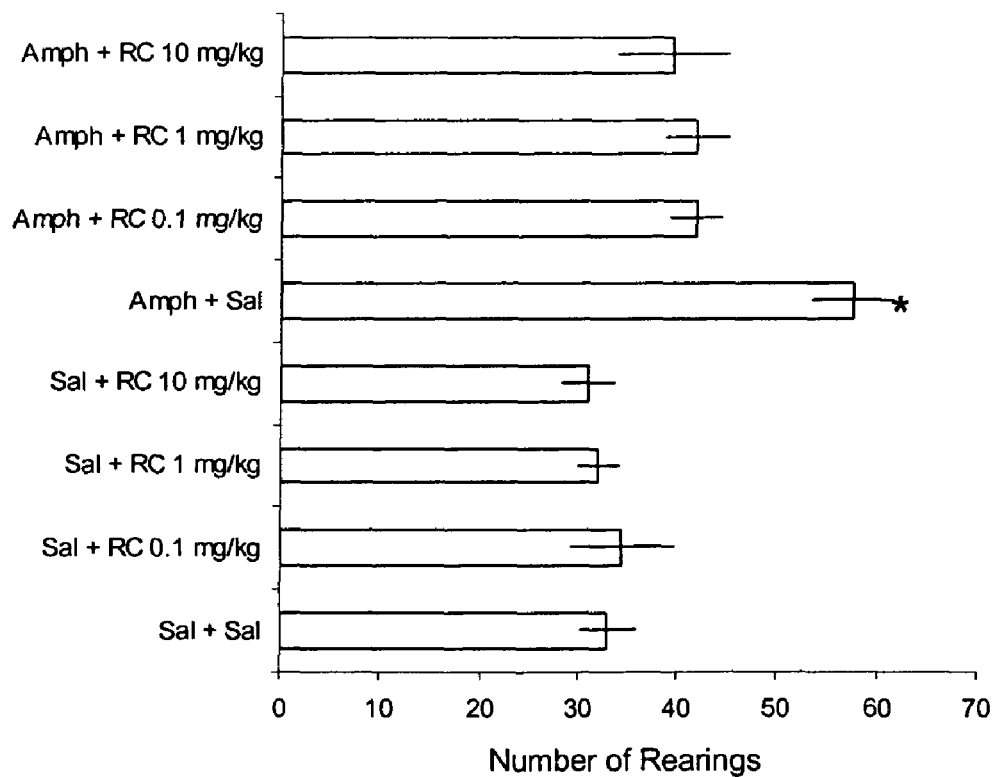

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Tpi
<220> FEATURE:
<221> NAME/KEY: MOD_RES
<222> LOCATION: (8)
<223> OTHER INFORMATION: Leu-psi
<220> FEATURE:
<223> OTHER INFORMATION: c-term amidation

<400> SEQUENCE: 1

Xaa Gln Trp Ala Val Gly His Leu Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 3-phenyl-propionyl-Gln
<220> FEATURE:
<221> NAME/KEY: MOD_RES
<222> LOCATION: (7)
<223> OTHER INFORMATION: Leu-psi
<220> FEATURE:
<221> NAME/KEY: MOD_RES
<222> LOCATION: (8)
<223> OTHER INFORMATION: Thz
<220> FEATURE:
<223> OTHER INFORMATION: c-term amidation

<400> SEQUENCE: 2

Gln Trp Ala Val Gly His Leu Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Phe, p-Hl-Phe, pGlu, Nal, Pal, Tpi or Trp
<220> FEATURE:
<221> NAME/KEY: MOD_RES
<222> LOCATION: (2)
<223> OTHER INFORMATION: Gln, Glu or His
<220> FEATURE:
<221> NAME/KEY: MOD_RES
<222> LOCATION: (8)
<223> OTHER INFORMATION: Leu-psi
<220> FEATURE:
<221> NAME/KEY: MOD_RES
<222> LOCATION: (9)
<223> OTHER INFORMATION: Tac, MTac or DMTac

<400> SEQUENCE: 3

Xaa Xaa Trp Ala Val Gly His Leu Xaa
1               5
```

USE OF BOMBESIN/GASTRIN-RELEASING PEPTIDE ANTAGONISTS FOR THE TREATMENT OF INFLAMMATORY CONDITIONS, ACUTE LUNG INJURY AND BIPOLAR DISORDER

REFERENCE TO RELATED CASES

This application claims priority to U.S. provisional application Ser. No. 60/636,525, filed Dec. 17, 2004, and to U.S. provisional application Ser. No. 60/748,178 filed Dec. 8, 2005, both incorporated herein by reference in their entirety.

FIELD OF THE INVENTION

The present invention relates to novel therapeutic strategies for the treatment of inflammatory and immune-mediated inflammatory conditions, in particular sepsis and acute lung injury, as well as bipolar disorder by means of the administration of bombesin/gastrin releasing peptide antagonists.

In addition, the invention concerns the use of a bombesin/gastrin releasing peptide antagonist in the preparation of a pharmaceutical composition for the treatment of inflammatory and immune-mediated inflammatory conditions, in particular sepsis, acute lung injury and rheumatoid arthritis as well as for the treatment or prophylaxis of brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder. In particular, specific nonapeptides with antagonist properties against bombesin or bombesin-like peptides, such as the gastrin releasing peptide, may be used in the treatment of inflammatory and immune-mediated inflammatory conditions as well as brain disorders.

BACKGROUND OF THE INVENTION

The bombesin/gastrin releasing peptide (GRP) receptor system, i.e. bombesin/gastrin, their receptors and the components of the receptor-mediated signaling pathways, is known to be involved in the regulation of several aspects of CNS function (Yamada et al., Mol. Psychiatry 7, 113-117 (2002)), in neuropsychiatric disorders, such as schizophrenia (Mellar et al., Peptides 25, 585-588 (2004)) and autism (Ishikawa-Brush et al., Hum. Mol. Genet. 6, 1241-1250 (1997)), in the development of cancer (Schwartsmann, G., Lung Cancer 46, 129 (2004); Szepeshazi et al., Proc. Natl. Acad. Sci. U.S.A. 94, 10913 (1997)), and in the pathogenesis of chronic bronchitis (Meloni et al., Int. J. Tissue React. 14, 195-201 (1992)) and pulmonary fibrosis (Lemaire et al., Neuropeptides 20, 63-72 (1991)).

It is further known that the bombesin/GRP system has several effects on the immune system. For example, GRP has been reported to induce mast cell proliferation and chemotaxis in vitro (Genton et al., American Journal of Surgery 186, 253-258 (2003); Subramaniam et al., Am. J. Respir. Crit. Care Med. 168, 601-611 (2003)) and to modulate, as a stimulator or inhibitor, the function of lymphocytes, phagocytes and natural killer cells (Medina et al., Mechanisms of Ageing and Development 102, 249-261 (1998); Medina et al., Neuropeptides 33, 173-179 (1999); De la Fuente et al., Immunology 73, 205-211 (1991); Medina et al., Neuropeptides 32, 549-555 (1998)). Furthermore, GRP seems to have stimulatory effects on mobility, ingestion and superoxide production in macrophages from adult mice, potentiating IL-1 release by alveolar macrophages activated with lipopolysaccharide (LPS) (De la Fuente et al., Life Sciences 67, 2125-2135 (2000); De la Fuente et al., Immunology 73, 205-211 (1991); Lemaire et al., Neuropeptides 20, 217-223 (1991)).

Although the exact intracellular pathways associated with the above-mentioned GRP-related effects remain to be identified it has been reported that certain GRP effects on murine peritoneal leukocytes are mediated through the activation of protein kinase C (Del Rio et al., Regul. Pept. 49, 185-193 (1994)). Further, it is known that bombesin, a homolog of GRP, stimulates cyclooxygenase-2 (COX-2) expression in intestinal epithelial cell lines. The bombesin-stimulated COX-2 expression requires an increase in $[Ca^{+2}]$, the activation of extracellular signal-regulated kinase (ERK)-1 and -2 and p38MAPK, and the increased activation and expression of the transcription factors Elk-1, ATF-2, c-Fos, and c-Jun (Guo Y.-S. et al., J. Biol. Chem. 276, 22941-22947 (2001)).

Over the past few years, the bombesin/GRP receptor system has emerged as a promising drug target for anticancer therapy (Schwartsmann, G., Lung Cancer 46, 129 (2004); Szepeshazi et al., Proc. Natl. Acad. Sci. U.S.A. 94, 10913 (1997), U.S. Pat. Nos. 5,244,883 and 5,369,094) and neuropsychiatric disorders (Ishikawa-Brush et al., Hum. Mol. Genet. 6, 1241-1250 (1997); and Mellar et al., Peptides 25, 585-588 (2004)) and great efforts have been directed to the development of bombesin/GRP antagonists. Today, several kinds of bombesin/GRP antagonists are known, which mainly belong to the class of polypeptide compounds. Examples thereof include nonapeptide compounds disclosed in U.S. Pat. No. 5,244,883, nonapeptide compounds disclosed in U.S. Pat. No. 5,369,094, analogues of substance P (Coy et al., J. Biol. Chem. 263, 5056 (1988)), and analogues of GRP(20-27) (Heimbrook et al., J. Biol. Chem. 264, 11258 (1989)).

The therapeutic potential of bombesin/GRP antagonists to improve inflammatory and immune-mediated inflammatory conditions, in particular septic shock and acute lung injury, however, is still unknown. The occurence of (systemic) inflammations is a serious problem associated with numerous medical conditions and is assumed to be the cause of death in many cases. The anti-inflammatory strategies available today, however, produce only modest clinical effects in critically ill patients (BLUE Journal). This could be secondary to several factors, including the heterogeneous inflammatory response associated with these conditions (Hotchkiss & Karl, New Engl. J. Med. 348, 138-150 (2003)) and the misleading design of pre-clinical studies (Ritter et al., Lancet 364, 498-499 (2004); Polderman et al., Lancet 363, 1721-1723 (2004)).

Septic shock, for example, has become one of the most frequent causes of morbidity and mortality in intensive care units (Sands et al., JAMA 278, 234-240 (1997)). Although commonly initiated by an infection, the pathogenesis of sepsis is characterized by an overwhelming systemic inflammatory response that can lead to lethal multiple organ failure (Hotchkiss & Karl, New Engl. J. Med. 348, 138-150 (2003)). Conventional treatment of sepsis consists of supporting blood pressure, organ blood flow and ventilation, along with an emphasis on antibiotics and eradicating the source(s) of infection. Despite significant advances in the understanding of pathogenesis of sepsis and its management, the mortality from septic shock has improved little over the last several decades (Friedman et al., Crit Care Med. 26, 2078-2086 (1998)).

Bipolar disorder, also known as manic-depressive illness, is a brain disorder that causes unusual shifts in a person's mood, energy, and ability to function. Different from the normal ups and downs that everyone goes through, the symptoms of bipolar disorder are severe. They can result in damaged relationships, poor job or school performance, and even suicide. A comprehensive overview about bipolar disorder and further references can be found in National Institute of Mental Health (NIMH) publication "Bipolar disorder", NIH Publication No. 02-3679, Printed 2001, Reprinted September 2002, which is also available at http://www.nimh.nih.gov/publicat/NIMHbipolar.pdf.

More than 2 million American adults, or about 1 percent of the population age 18 and older in any given year, have bipolar disorder. Bipolar disorder typically develops in late adolescence or early adulthood. However, some people have their first symptoms during childhood, and some develop them late in life. It is often not recognized as an illness, and people may suffer for years before it is properly diagnosed and treated. Like diabetes or heart disease, bipolar disorder is a long-term illness that must be carefully managed throughout a person's life.

Bipolar disorder causes dramatic mood swings—from overly "high" and/or irritable to sad and hopeless, and then back again, often with periods of normal mood in between. Severe changes in energy and behavior go along with these changes in mood. The periods of highs and lows are called episodes of mania and depression.

Signs and symptoms of mania (or a manic episode) include "Increased energy, activity, and restlessness; Excessively "high," overly good, euphoric mood; Extreme irritability; Racing thoughts and talking very fast, jumping from one idea to another; Distractibility, can't concentrate well; Little sleep needed; Unrealistic beliefs in one's abilities and powers; Poor judgment; Spending sprees; A lasting period of behavior that is different from usual; Increased sexual drive; Abuse of drugs, particularly cocaine, alcohol, and sleeping medications; Provocative, intrusive, or aggressive behavior; Denial that anything is wrong".

A manic episode is diagnosed if elevated mood occurs with three or more of the other symptoms most of the day, nearly every day, for 1 week or longer. If the mood is irritable, four additional symptoms must be present.

Signs and symptoms of depression (or a depressive episode) include "Lasting sad, anxious, or empty mood; Feelings of hopelessness or pessimism; Feelings of guilt, worthlessness, or helplessness; Loss of interest or pleasure in activities once enjoyed, including sex; Decreased energy, a feeling of fatigue or of being "slowed down"; Difficulty concentrating, remembering, making decisions; Restlessness or irritability; Sleeping too much, or can't sleep; Change in appetite and/or unintended weight loss or gain; Chronic pain or other persistent bodily symptoms that are not caused by physical illness or injury; Thoughts of death or suicide, or suicide attempts".

A depressive episode is diagnosed if five or more of these symptoms last most of the day, nearly every day, for a period of 2 weeks or longer.

A mild to moderate level of mania is called hypomania. Hypomania may feel good to the person who experiences it and may even be associated with good functioning and enhanced productivity. Thus even when family and friends learn to recognize the mood swings as possible bipolar disorder, the person may deny that anything is wrong. Without proper treatment, however, hypomania can become severe mania in some people or can switch into depression.

Sometimes, severe episodes of mania or depression include symptoms of psychosis (or psychotic symptoms). Common psychotic symptoms are hallucinations (hearing, seeing, or otherwise sensing the presence of things not actually there) and delusions (false, strongly held beliefs not influenced by logical reasoning or explained by a person's usual cultural concepts). Psychotic symptoms in bipolar disorder tend to reflect the extreme mood state at the time. For example, delusions of grandiosity, such as believing one is the President or has special powers or wealth, may occur during mania; delusions of guilt or worthlessness, such as believing that one is ruined and penniless or has committed some terrible crime, may appear during depression. People with bipolar disorder who have these symptoms are sometimes incorrectly diagnosed as having schizophrenia, another severe mental illness.

It may be helpful to think of the various mood states in bipolar disorder as a spectrum or continuous range. At one end is severe depression, above which is moderate depression and then mild low mood, which many people call "the blues" when it is short-lived but is termed "dysthymia" when it is chronic. Then there is normal or balanced mood, above which comes hypomania (mild to moderate mania), and then severe mania.

In some people, however, symptoms of mania and depression may occur together in what is called a mixed bipolar state. Symptoms of a mixed state often include agitation, trouble sleeping, significant change in appetite, psychosis, and suicidal thinking. A person may have a very sad, hopeless mood while at the same time feeling extremely energized.

Bipolar disorder may appear to be a problem other than mental illness—for instance, alcohol or drug abuse, poor school or work performance, or strained interpersonal relationships. Such problems in fact may be signs of an underlying mood disorder.

The prevalence, high risk for suicide and social and economic costs reveal bipolar disorder as a major public health hazard.

There is a need, therefore, for alternative medicaments for the treatment of inflammatory and immune-mediated inflammatory conditions, such as sepsis and acute lung injury, as well as bipolar disorder.

SUMMARY OF THE INVENTION

The present invention provides a bombesin/gastrin-releasing peptide (GRP) antagonist suited for the preparation of a pharmaceutical composition for the treatment of inflammatory and immune-mediated inflammatory conditions as well as brain disorders, in particular bipolar disorder. The bombesin/GRP antagonist of the invention is particularly useful for the treatment of sepsis and acute lung injury and the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder.

The present invention is based on the unexpected finding that, in vivo, treatments with bombesin/GRP antagonists attenuate serum TNF-α and IL-1β-levels and improve survival in inflammatory conditions, in particular in "established" sepsis, even when the treatment is initiated after the onset of the disease. In addition, the bombesin/GRP antagonists according to the present invention diminish the lung damage induced by the intra-tracheal instillation of lipopolysaccharide (LPS) in an established model of acute lung injury (ALI). Thus, the bombesin/GRP antagonist of the present invention provides an alternative therapeutic strategy for the treatment of inflammatory and immune-mediated inflammatory conditions, in particular sepsis and acute lung injury.

The present invention is further based on the unexpected finding that, in vivo, treatments with bombesin/GRP antagonists prevent d-amphetamine induced hyperactivity in an established model of acute mania/bipolar disorder. Thus, the bombesin/GRP antagonist of the present invention provides an alternative therapeutic strategy for the treatment or prophylaxis of brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder.

According to the invention the used bombesin/GRP antagonists belong to the class of polypeptide compounds and are preferably nonapeptide as those disclosed in U.S. Pat. Nos. 5,244,883 and 5,369,094. Most preferably the antagonist of the invention is H-D-Tpi-Gln-Trp-Ala-Val-Gly-His-Leu-psi-Leu-$NH_2$ (SEQ ID NO: 1) (in the following denoted as RC-3095) or 3-phenyl-propionyl-Gln-Trp-Ala-Val-Gly-His-Leu-psi-Thz-$NH_2$ (SEQ ID NO: 2) (in the following denoted as RC-3940-II).

In a preferred embodiment of the invention two or more different bombesin/GRP antagonists are used in the preparation of a pharmaceutical composition for the treatment of inflammatory and immune-mediated inflammatory conditions.

In another preferred embodiment of the invention two or more different bombesin/GRP antagonists are used in the preparation of a pharmaceutical composition for the treatment or prophylaxis of brain disorders, preferably bipolar disorder, and in particular the different forms and/or subforms of bipolar disorder.

In a further preferred embodiment the bombesin/GRP antagonist of the invention or a pharmaceutically acceptable salt thereof is administered to a patient in a daily amount of 0.01 to 10 mg per kg body weight, wherein the preferred route of administration is subcutaneously.

In a further embodiment the bombesin/GRP antagonists of the invention are suitable for use in a combination with other drug products for the treatment of inflammatory and immune-mediated inflammatory conditions.

In a yet further embodiment the bombesin/GRP antagonists of the invention are suitable for use in a combination with other drug products for the treatment or prophylaxis of brain disorders, preferably bipolar disorder, and in particular the different forms and/or subforms of bipolar disorder.

The description may be understood more fully by reference to the following detailed description of the invention, the example and the appended figures described below:

BRIEF DESCRIPTION OF THE FIGURES

FIG. 5 shows protein carbonyls and thiobarbituric acid reactive species content in the lung after acute lung injury induced by lipopolysaccharide (LPS). Rats were exposed to LPS or saline and treated with RC-3095 as described in the Example. 24 hours after acute lung injury induction the lung was removed to the determination of protein carbonyls and thiobarbituric acid reactive species content as described in the Example. Values are expressed as means±S.D. (n=6 each group).
different from saline, $p<0.05$
different from LPS, $p<0.05$ FIG. 6 shows the prevention of amphetamine (AMPH)-induced hyperactivity in rats by RC-3095. Data are mean±SEM number of crossings and rearings performed during exploration of an open field. Animals were given a 10 ml/kg i.p. injection of saline (SAL, 0.9% NaCl) or RC-3095 (0.1, 1.0 or 10.0 mg/kg) followed by an i.p. injection of SAL or amphetamine (AMPH, 2 mg/kg). * $p<0.05$, significant difference from the control group treated with two injections of SAL.

Throughout the drawings, the same or like elements are designated with the same reference sign to ease understanding of the invention.

DETAILED DESCRIPTION

Figure 1:
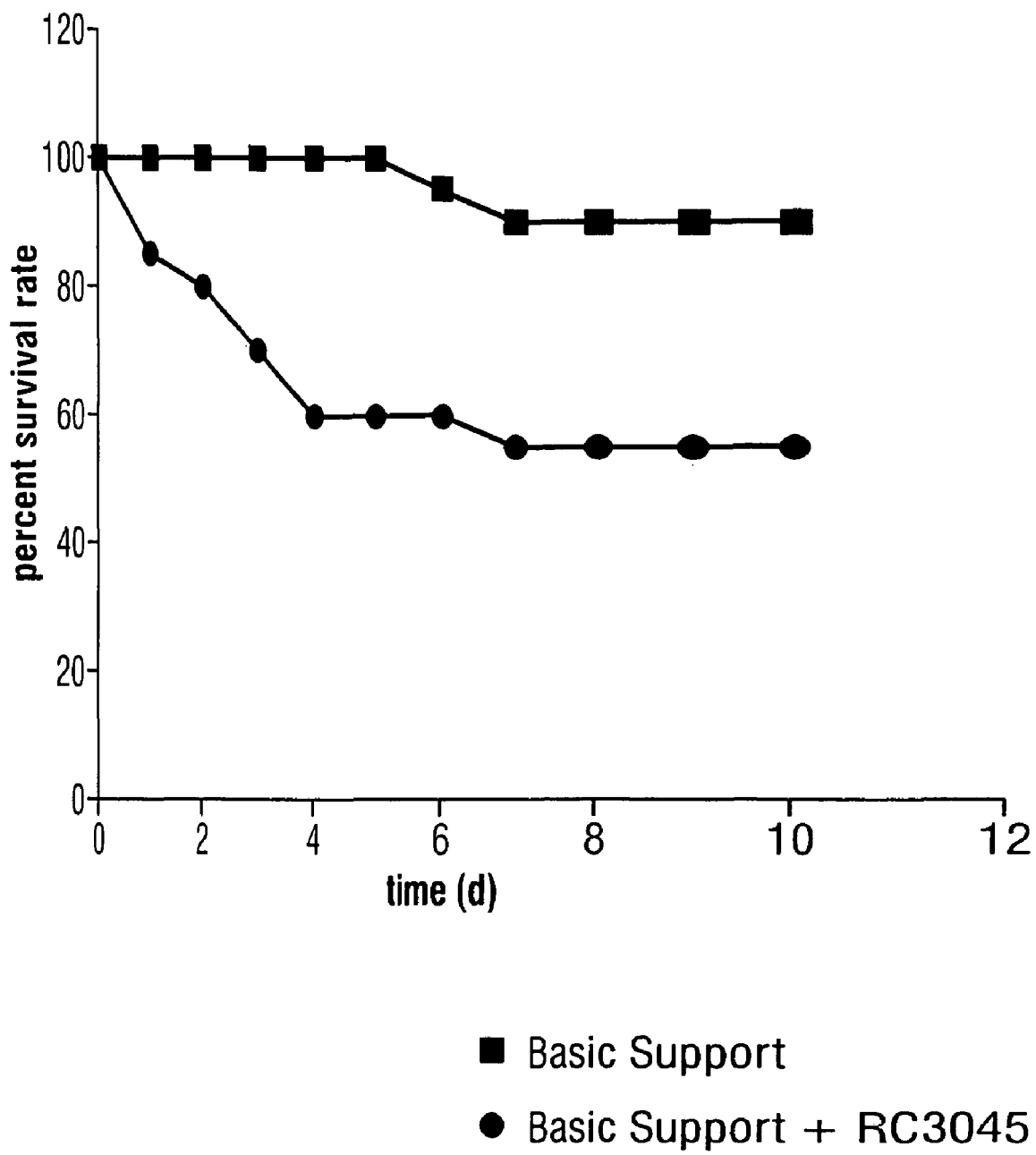
FIG. 1 shows the effect of the gastrin release peptide (GRP) receptor antagonist RC-3045 on survival in established sepsis. Adult male Wistar rats were subjected to cecal ligation and perforation (cecal ligation puncture, CLP) and two groups were defined in a double-blind, randomized design: 1) basic support (ceftriaxone 30.0 mg/kg every 6 h plus clindamycin 25.0 mg/kg every 6 h for three days, plus saline reposition 30 ml/kg every 12 h in the first day); 2) basic support plus RC-3095 treatment (5 mg/kg once a day for two days). All treatments started 6 h after surgical procedure. Survival was recorded in a 10-day period. Data are shown as percent of animals surviving (n=32 in group 1 and n=40 in group 2; *$p<0.01$ Kaplan-Meier curve; cox-regression analyses).

The present invention relates to the use of a bombesin/gastrin releasing peptide antagonist the preparation of a pharmaceutical composition for the treatment of inflammatory and immune-mediated inflammatory conditions, preferably sepsis and acute lung injury.

The present invention further relates to the use of a bombesin/gastrin releasing peptide antagonist in the preparation of a pharmaceutical composition for the treatment or prophylaxis of brain disorders, preferably bipolar disorder, and in particular the different forms and/or subforms of bipolar disorder.

In accordance with the present invention, it is to be understood, that the term "inflammatory condition" or "immune-mediated inflammatory condition" respectively, when used herein, means any disease state which involves inflammatory processes, i.e. processes which involve cells of the immune system, such as T- and B-lymphocytes, macrophages, mast cells, natural killer cells, etc. with or without the concomitant production of interleukines and/or cytokines. Thus, within the context of the present invention, it is to be understood, that the medical conditions "sepsis" and "acute lung injury", but also "septic shock", "rheumatoid arthritis", "colitis ulcerative", "Crohn's disease", "oncologic inflammatory infiltration", "psoriatic arthritis", and other diseases fall within the definition of "inflammatory condition" or "immune-mediated inflammatory condition" since all involve inflammatory reactions. In the case of sepsis, for example, the pathogenesis is characterized by an overwhelming systemic inflammatory response that can lead to lethal multiple organ failure.

In accordance with the present invention, it is further to be understood, that the term "bipolar disorder" or "different forms and/or subforms of bipolar disorder" respectively, when used herein, comprise any state or condition which is known to be part of, involved in, show symptoms of etc. bipolar disorder and its various forms and/or subforms. Thus, within the context of the present invention, it is to be understood, that the medical conditions "mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder" and other states or conditions fall within the definition of "bipolar disorder" or "different forms and/or subforms of bipolar disorder" since all are involved in or are specific forms of bipolar disorder.

Furthermore, the present invention provides, that the terms "a treatment of a condition, state, disease or disorder", when used herein, also covers the actual therapy as well as maintenance therapy and prophylaxis against recurrence of human beings as well as mammals.

According to a preferred embodiment of the present invention the polypeptide compounds disclosed in U.S. Pat. No. 5,244,883, CA 2,097,192 or WO 92/09626 having antagonist properties against bombesin or bombesin-like peptides, such as GRP, Neuromedin C and the like, may be used as bombesin/GRP antagonist. These bombesin/GRP antagonists of the present invention are represented by the following general formula (I):

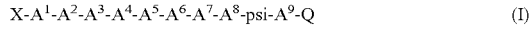
$$X-A^1-A^2-A^3-A^4-A^5-A^6-A^7-A^8\text{-psi-}A^9-Q \qquad (I)$$

wherein

Q is $NH_2$ or $OQ^1$, where $Q^1$ is hydrogen, $C_{1-10}$-alkyl, phenyl or phenyl-$C_{7-10}$-alkyl;

X is hydrogen, a single bond linking the alpha amino group of $A^1$ to the side chain carboxyl group, where present of $A^2$, or a group of formula $R^1CO$—, wherein $R^1$ is selected from the groups consisting of (a) hydrogen, $C_{1-10}$-alkyl, phenyl or phenyl-$C_{7-10}$-alkyl; (b) $R^2(R^3)N$—, wherein $R^2$ is hydrogen, $C_{1-10}$-alkyl, phenyl or phenyl-$C_{7-10}$-alkyl, $R^3$ is hydrogen or $C_{1-10}$-alkyl; and (c) $R^4$—O—, wherein $R^4$ is $C_{1-10}$-alkyl, phenyl or phenyl-$C_{7-10}$-alkyl;

$A^1$ is D-, L- or DL-pGlu, Nal, Phe, Thi, Tyr, Tpi, Hca, Hpp, Mpp, Trp or Trp substituted in the benzene ring by one or more members selected from the group consisting of halogen, $NO_2$, $NH_2$, OH, $C_{1-3}$-alkyl and $C_{1-3}$-alkoxy wherein halogen is fluorine, chlorine and bromine;

$A^2$ is Asn, Dpa, Gln, His, MeHis, His(Bz), His(Z) or a group of formula Dpa(X), Asp(Y), Glu[-] and Glu(Y), wherein X is as above, Y is —$OR^5$ or —$N(R^6)R^7$ wherein $R^5$ is hydrogen, $C_{1-3}$-alkyl or phenyl;, $R^6$ is hydrogen or $C_{1-3}$-alkyl;

$R^7$ is hydrogen, $C_{1-3}$-alkyl or —$NHCONH_2$, and

[-] is a single bond linking the side carboxyl group, where present of $A^2$ with the alpha amino group of $A^1$ where X is a single bond;

$A^3$ is Nal, Pal, Tpi, Trp, MeTrp, Trp(For) or Trp substituted in the benzene ring by one or more members selected from the group consisting of halogen, $NO_2$, $NH_2$, OH, $C_{1-3}$-alkyl and $C_{1-3}$-alkoxy wherein halogen is fluorine, chlorine and bromine;

$A^4$ is Ala, MeAla or Gln;

$A^5$ is Val or MeVal;

$A^6$ is Gly, Phe or D-Ala;

$A^7$ is His, MeHis, His(Bz), His(Z), Lys(Z) or Pal;

$A^8$ is a reduced isostere of Leu or Phe;

$A^9$ is Leu, Phe, Tpi, Trp or Trp substituted in the benzene ring by one or more members selected from the group consisting of halogen, $NO_2$, $NH_2$, OH, $C_{1-3}$-alkyl and $C_{1-3}$-alkoxy wherein halogen is fluorine, chlorine and bromine;

provided that where $A^9$ is Leu or Phe, $A^1$ is other than D-Nal or DL-Phe and where $A^1$ is D-Nal or DL-Phe, $A^9$ is other than Leu or Phe; and the salts thereof with pharmaceutically acceptable acids.

Among the above compounds of formula (I) the compound H-D-Tpi-Gln-Trp-Ala-Val-Gly-His-Leu-psi-Leu-NH2 (SEQ ID NO: 1) (RC-3095) is most preferably used within the context of the present invention.

According to another preferred embodiment of the present invention the polypeptide compounds disclosed in U.S. Pat. No. 5,369,094 may be used as bombesin/GRP antagonists. These bombesin/GRP antagonists of the present invention are represented by the following general formula (II) (SEQ ID NO: 3):

$$X-A1-A2-\text{Trp-Ala-Val-Gly-His-Leu-psi-}A9-Q \qquad (II)$$

wherein

Q is $NH_2$ or —$OQ^1$ where $Q^1$ is hydrogen, $C_{1-10}$-alkyl, phenyl or phenyl-$C_{1-10}$-alkyl;

X is hydrogen or a single bond linking the alpha amino group of $A^1$ to the gamma carboxyl moiety on the 3-propionyl moiety of $A^2$ when $A^2$ is Glu[-], or a group of formula $R^1CO$—, wherein $R^1$ is selected from the groups consisting of (a) hydrogen, $C_{1-10}$-alkyl, phenyl, phenyl-$C_{1-10}$-alkyl, p-HI-phenyl, p-HI-phenyl-$C_{1-10}$-alkyl, naphthyl, naphthyl-$C_{1-10}$-alkyl, indolyl, indolyl-$C_{1-10}$-alkyl, pyridyl, pyridyl-$C_{1-10}$-alkyl, thienyl, thienyl-$C_{1-10}$-alkyl, cyclohexyl or cyclohexyl-$C_{1-10}$-alkyl, where HI is F, Cl, Br, OH, $CH_3$ or $OCH_3$; (b) $R^2(R^3)N$—, wherein $R^2$ is hydrogen, $C_{1-10}$-alkyl, phenyl or phenyl-$C_{1-10}$-alkyl, $R^3$ is hydrogen or $C_{1-10}$-alkyl; (c) $R^4$—O— wherein $R^4$ is $C_{1-10}$-alkyl, phenyl or phenyl-$C_{1-10}$-alkyl;

$A^1$ is D- or L-amino acid residue selected from the group consisting of Phe, p-HI-Phe, pGlu, Nal, Pal, Tpi, Trp or Trp substituted in the benzene ring by one or more members selected from the group consisting of halogen, $NH_2$, or $C_{1-3}$-alkyl; or $A^1$ is a peptide bond linking the acyl moiety of $R^1CO$— to the alpha amino moiety of $A^2$; provided $X=R^1CO$—;

$A^2$ is Gln, Glu[-], Glu(Y) or His, wherein [-] is a single bond, when X is a single bond and $A^2$ is Glu[-], said [-] linking the gamma carboxyl moiety on the 3-propionyl moiety of said $A^2$ with the alpha amino group of $A^1$, Y is (a) —$OR^5$, wherein $R^5$ is hydrogen, $C_{1-10}$-alkyl or phenyl; or (b) —$N(R^6)R^7$, wherein $R^6$ is hydrogen or $C_{1-3}$-alkyl, $R^7$ is hydrogen, $C_{1-3}$-alkyl or —$NHCONH_2$, and Leu-psi- is a reduced form of Leu wherein the C=O moiety is instead —$CH_2$— such that the bond of this —$CH_2$— moiety with the alpha amino group of the adjacent $A^9$ residue is a pseudopeptide bond;

$A^9$ is Tac, MTac, or DMTac; and the salts thereof with pharmaceutically acceptable acids.

Among the above compounds of formula (II) the compound 3-phenyl-propionyl-Gln-Trp-Ala-Val-Gly-His-Leu-psi-Thz-NH2 (SEQ ID NO: 2) (RC-3940-II) is most preferably used within the context of the present invention.

According to the invention, the compounds according to formula (I) or (II) may be present in the form of pharmaceutically acceptable salts or acids. Examples thereof include acid addition salts selected from hydrochlorides, sulphates, maleates, tartrates and the like, preferably acetates, embonates and trifluoroacetates.

In a further preferred embodiment of the present invention, one or more bombesin/GRP antagonists as defined above, particularly RC-3095, are used to prepare a pharmaceutical composition for the prevention of brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder, where the bombesin/GRP antagonists, and in particular RC-3095, act as a mood-stabilizer, in particular anti-maniac agent, that can also prevent new episodes of bipolar disorder, such as mania and/or depression and/or their different subforms.

In a further preferred embodiment of the present invention, a mixture of two or more different bombesin/GRP antagonists as defined above may be used to prepare a pharmaceutical composition for combating inflammatory and immune-mediated inflammatory conditions and/or brain disorders, preferably bipolar disorder, and/or in particular the different forms and/or subforms of bipolar disorder. For example, in the treatment of inflammatory and immune-mediated inflammatory conditions and/or treatment or prophylaxis of brain disorders, preferably bipolar disorder, and/or in particular the different forms and/or subforms of bipolar disorder, the applied bombesin/GRP antagonist can be RC-3095 or RC-3940-II with or without one or more other bombesin/GRP antagonists according to the invention, wherein said antagonists are also applicable as a pharmaceutical kit. The pharmaceutical composition of the invention may also contain further active ingredients/medicaments for the same or other diseases depending on the inflammatory conditions and/or brain disorders to be treated.

The bombesin/GRP antagonists of the invention are suitable for use in a combination with other drug products for the treatment of inflammatory and immune-mediated inflammatory conditions. Such drug products are applied before and/or during and/or after the treatment with the bombesin/GRP antagonists of the invention. The drug products are also applicable together with the bombesin/GRP antagonists as a pharmaceutical kit.

Such other drug products may be:

Nonsteroidal anti-inflammatory drugs (NSAIDs). They may be selected from but not restricted to aspirin, indomethacin, ibuprofen and COX-2 inhibitors like celecoxib and valdecoxib.

Analgesic drugs. They may be selected from but not restricted to acetaminophen, propoxyphene, mepeidine, morphine.

Glucocorticoids or prednisone.

Disease modifying antirheumatic drugs (DMARDs). They may be selected from but not restricted to azathioprine, penicillamine, chloroquine, hydroxychloroquine, sulfasalazine, methotrexate, injectable and oral gold.

Biologic response modifiers. They may be selected from but not restricted to anakinra, adaliumumab, etanercept, infliximab.

The bombesin/GRP antagonists of the invention are further suitable for use in a combination with other drug products for the treatment or prophylaxis of brain disorders, preferably bipolar disorder, and/or in particular the different forms and/or subforms of bipolar disorder. Such drug products are applied before and/or during and/or after the treatment with the bombesin/GRP antagonists of the invention. The drug products are also applicable together with the bombesin/GRP antagonists as a pharmaceutical kit.

In this respect, such other drug products may be for instance "mood stabilizers" usually prescribed to help control bipolar disorder. Several different types of mood stabilizers are available. In general, people with bipolar disorder continue treatment with mood stabilizers for extended periods of time (years). Other medications are added when necessary, typically for shorter periods, to treat episodes of mania or depression that break through despite the mood stabilizer.

Non-limiting examples of such mood-stabilzers are:

Lithium

Anticonvulsant medications, such as valproate (Depakote®) or carbamazepine (Tegretol®)

Newer anticonvulsant medications, including lamotrigine (Lamictal®), gabapentin (Neurontin®), and topiramate (Topamax®)

Atypical antipsychotic medications, including clozapine (Clozaril®), olanzapine (Zyprexa®), risperidone (Risperdal®), quetiapine (Seroquel®), and ziprasidone (Geodon®)

benzodiazepine medication such as clonazepam (Klonopin®) or lorazepam (Ativan®)

sedative medications, such as zolpidem (Ambien®)

The pharmaceutical composition of the invention suitable for the treatment of inflammatory and immune-mediated inflammatory conditions, such as sepsis, acute lung injury, septic shock, rheumatoid arthritis, colitis ulcerative, Crohn's disease, oncologic inflammatory infiltration, psoriatic arthritis, and/or for the treatment or prophylaxis of brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder, contains at least one bombesin/GRP antagonist as active ingredient as mentioned above. In addition to the at least one bombesin/GRP antagonist, the pharmaceutical composition of the invention may contain suitable pharmaceutically acceptable carriers, diluents and/or adjuvans, which facilitate processing of the active ingredient into preparations and/or determine the pharmacokinetics. Further details on techniques for formulation of pharmaceutical preparations are well-known to a person skilled in the art.

The bombesin/GRP antagonist is contained in the pharmaceutical composition of the invention suited for the treatment of inflammatory and immune-mediated inflammatory diseases and/or brain disorders in a therapeutically effective amount to achieve the intended purpose. The actual total dose of the respective bombesin/GRP antagonist(s) contained in the pharmaceutical composition to be administered for the treatment depends, for example, on the nature and stage of the mentioned disease, the age and sex of the patient, the nature of the administration and the duration of the treatment. For the pharmaceutical composition of the invention, a daily dosage of 0.01 to 10 mg per kg body weight, preferably 0.015 to 1.5 mg per kg body weight, more preferably 0.03 to 0.3 mg per kg body weight of the at least one bombesin/GRP antagonists is suitable, wherein the daily dosages of the bombesin/GRP antagonist can be administered at once or in two or more subdosages.

The pharmaceutical preparation according to the present invention may be administered as a liquid, semi-solid or solid drug form as solutions, suspensions, emulsions, gels, ointments, foams, pastes, aerosols, powders, and others. Suitable routes of administration may, for example, include dermally, intravenously, intramuscularly, subcutaneously, intrasanally and the like administrations. The preferred route of administration is subcutaneously. Preferably, the subject being treated is an animal, preferably a mammal, and most preferably a human being.

The period of action of the compounds of the invention, such as the compounds according to general formula (I) or general formula (II), can be prolonged by suitable measures with respect to practical therapeutic requirements. This objective can be achieved by chemical or pharmaceutical means. Examples of achieving a prolongation of the period of action are the use of implant and liposomes, the formation of salts and complexes of low solubility or the use of crystalline suspensions.

The present invention is explained in more detail by means of the following examples without, however, being restricted thereto.

EXAMPLES

I)

Here, the inventors of the present invention demonstrate the therapeutic potential of the bombesin/GRP antagonist RC-3095 for the treatment of the inflammatory condition rheumatoid arthritis.

They further demonstrate the therapeutic potential of the bombesin/GRP antagonist RC-3095 for the treatment of two inflammatory conditions, namely sepsis and acute lung injury. Experiments directed to the effect of RC-3095 on macrophages revealed that RC-3095 attenuates the release of the pro-inflammatory cytokines TNF-α and IL-1β by activated macrophages.

In vivo, the treatment with the bombesin/GRP receptor antagonist RC-3095 attenuates serum TNF-α and IL-1β levels in a well-established model for experimental sepsis and improves survival in inflammatory conditions, in particular in "established" sepsis, even when the treatment is initiated after the onset of the disease. Futhermore, it was found that the bombesin/GRP receptor antagonist RC-3095 diminishs the lung damage induced by the intra-tracheal instillation of lipopolysaccharide (LPS) in an established model of acute lung injury (ALI).

In addition, the bombesin/GRP antagonist RC-3095 was shown to attenuate oxidative damage in several organs associated with the sepsis response and lung oxidative damage in ALI. It is well-known that reactive oxygen species (ROS) exhibit several proinflammatory properties pertinent to septic shock (Salvemini et al., *Br. J. Pharmacol.* 127, 685-692 (1999); Fantone & Ward, *Am. J. Pathol.* 107, 395-418 (1982); Ritter et al., Oxidative parameters and mortality in sepsis induced by cecal ligation and perforation, *Int. Care Med.* (2003)). Besides its pro-inflammatory effects, ROS possess a number of cytotoxic mechanisms, and induces the activation of the nuclear enzyme poly(adenosine 5'-diphosphate-ribose) polymerase, depletion of nicotinamide adenine dinucleotide (NAD) and adenosine triphosphate (ATP), which leads to irreversible cellular damage as evidenced in septic shock (Scabó et al., *Trends Pharmacol. Sci.* 19, 287-298 (1999)). Antioxidants inhibit the release of TNF, the activation of proinflammatory cytokines, cellular apoptosis and necrosis (Peristeris et al., *Cell Immunol.* 140, 390-399 (1992)).

Moreover, RC-3095 could attenuate the inflammatory infiltration, intestinal bacterial translocation and these effects could, in part, be responsible to the protective effects demonstrated. The experimental data suggest that RC-3095 did not exhibit direct antioxidant or antibiotic effects.

Thus, the following experimental results represents the identification of novel therapeutic strategies for the treatment of inflammatory and immune-mediated inflammatory diseases, in particular sepsis, acute lung injury, septic shock, rheumatoid arthritis, colitis ulcerative, Crohn's disease, oncologic inflammatory infiltration, psoriatic arthritis and other diseases.

I.1. Examplary Embodiment
RC-3095 Composition

| Ingredients | Quantity/Unit |
| --- | --- |
| RC-3095 acetate salt | approx. 6.36 mg to 7.17 mg (corresponding to 6 mg RC-3095 base) |
| delta lactone gluconic acid | approx. 3.5 mg |
| mannitol | approx. 96 mg |
| Total weight per unit: | approx. 106.27 mg |

The composition consists of a white lyophilised cake in a 4 ml injection vial. One injection vial will be reconstituted with 2 ml water for injection.

Administration

A female patient with rheumatoid arthritis, 49 years old, started on March 22 with 6 mg of RC-3095, twice daily. Application subcutaneously.

At baseline visit the patient presented with joint pain grade 3, joint inflammation grade 2 and depression grade 2.

Before start with RC-3095 she was already taken methotrexate, subcutaneously, once a week, and corticosteroids.

She was followed every two weeks by physical examination and laboratorial exams.

After approximately one week using RC-3095 she improved her symptoms and her quality of life. The adverse events were only local (nodes and pruritus).

Disease activity score—DAS:
Visit March 22: DAS=6.69
Visit March 29: DAS=7.20

I.2. Experimental Procedures

In vivo studies were performed in accordance with National Institutes of Health guidelines and with the approval of the local ethics committee of Brazil. All experiments were carried out using experimental models in rats.

I.2.1 Cecal Ligation Puncture (CLP) Model

Male Wistar rats 2-3 month old, subjected to cecal ligation puncture (CLP) as previously described (Ritter et al., *Crit. Care Med.* 32, 342-349 (2004)), were used in this study. The rats were anesthetized with a mixture of ketamine (80 mg/kg) and xylazine (10 mg/kg), given intraperitoneally. Under aseptic conditions, a 3-cm midline laparotomy was performed to allow exposure of the cecum with adjoining intestine. The cecum was tightly ligated with a 3.0 silk suture at its base, below the ileocecal valve, and was perforated once with a 14-gauge needle. The cecum was then gently squeezed to extrude a small amount of feces from the perforation site. The cecum was then returned to the peritoneal cavity and the laparotomy was closed with 4.0 silk sutures. The septic rats in this model become bacteremic with gram-negative enteric organisms (Roesler et al., *Trends Pharmacol. Sci.* 25, 241-242 (2004)).

For the purpose of biochemical measurements and histopathological analyses (see below), 24 rats were made septic by CLP. The animals were divided into four groups; 1—sham operated, or 2—CLP, or 3—CLP plus "basic support" (saline s.c. at 50 ml/kg 6 h and 12 h after CLP plus ceftriaxone s.c. at 30 mg/kg and clindamycin s.c. 25 mg/kg every 6 h for three days, starting 6 h after CLP), and 4—same as group 3 with RC-3095 s.c at 5 mg/kg, once a day for two days, starting 6 h after CLP. Blood was drawn from the caudal vein 3 and 12 hours after CLP to the determination of biochemical plasmatic markers (see below). Twenty four hours after treatment administration the rats were killed by decapitation followed by the harvesting of samples from the blood (by cardiac puncture), lung, liver, kidney, heart, ileum and mesenteric lymph nodes that were immediately stored at −70° C. until assayed for thiobarbituric acid reactive species (TBARS) and protein carbonyl formation (as an index of oxidative damage), or were fixed for posterior histophatological analyses (see below).

As an index of oxidative stress the formation of thiobarbituric acid reactive species (TBARS) during an acid-heating reaction as previously described was used. Briefly, the sample was mixed with trichloroacetic acid 10% and thiobarbituric acid 0.67% (Sigma Chemical, St. Louis, Mo.) and then heated in a boiling water bath for 15 min. TBARS was determined by the absorbance at 535 nm using 1,1,3,3-tetramethoxy-propane as an external standard. Results are expressed as malondialdehyde equivalents per milligram of protein (Lowry assay). In addition we determined the oxidative damage to proteins as previously described. Briefly, protein were precipitated by the addition of 20% trichloroacetic acid and redissolved in dinitrophenylhydrazine (Sigma Chemical, St. Louis, Mo.) and the absorbance read at 370 nm.

Serum TNF-α, IL-1β and IL-10 levels were determined 24 h after CLP by ELISA with commercial available kits (R&D systems, Minneapolis, Minn.). Serum markers of organ damage (aspartate aminotransferase (AST), serum glutamate pyruvate transaminase (ALT, synonym for serum glutamate pyruvate transminase (SGPT)), urea, creatinine, amylase, lipase) were determined 3 h, 12 h and 24 h after CLP by commercial available kits (Labtest, São Paulo, Brazil). All these analyses were performed by investigators blinded to the treatment. For histopathological analyses after fixation, excised liver tissues were embedded in paraffin and then routinely stained with hematoxylin and eosin. A blinded experienced pathologist performed histopathological analyses.

As an index to intestinal bacteria translocation the mesenteric lymph nodes from each animal were collected and homogenized. Serial ten-fold dilutions of the homogenates were plated onto blood agar plates and incubated for 24 h at 37° C. The colonies that appeared were counted to determine the number of bacteria per gram of lymph nodes.

Survival was tested in a separated cohort of animals. In a first protocol, animals exposed to CLP were randomly assigned to receive the bombesin/GRP antagonist RC-3095 1 h before (n=22), or 1 h after (n=25) CLP induction without "basic support". In a second set of experiments, the effect of RC-3095 with "basic support" was analyzed to more closely resemble clinical practice. The animals were challenged with CLP and with "basic support" (n=32) (saline s.c. at 50 ml/kg 6 h and 12 h after CLP plus ceftriaxone s.c. at 30 mg/kg and clindamycin s.c. 25 mg/kg every 6 h for three days, starting 6 h after CLP) or with "basic support" with RC-3095 (n=40) (s.c at 5 mg/kg, once a day for two days, starting 6 h after CLP). In all these experiments a sham-operated group and a CLP group without treatment were included to comparison. The mortality of the animals was recorded over a 10 day period.

I.2.2 ALI (Acute Lung Injury) Model

Adult male Wistar rats weighing approximately 250 to 300 g were used in this study. The rats were anesthetized by an intraperitoneal injection of ketamine (80 mg/kg) and acute respiratory distress syndrome (ARDS) was induced by intratracheal instillation of lipopolysaccharide (LPS) (*Escherichia coli* 055:B5; Sigma Chemical, St. Louis, Mo.) at a dose of 100 μg/100 g body weight.

Twelve hours after LPS instillation, the rats were killed and a bronchoalveolar lavage (BAL) was performed as previously described. The BAL fluid (BALF) was centrifuged (1000 g for 10 min) and the resultant cell-free supernatant was analyzed for the different biochemical parameters (see below). The cell pellet used to determine the total cell count and differential (see below). In a separated cohort of animals ARDS was induced as described above to isolate lung tissue. Twelve hours after LPS instillation, the rats were killed and samples from the lung were isolated and immediately stored at −70° C. until assayed for oxidative stress parameters or fixed in 4% formalin solution for histopathological analyses as described above.

The animals were divided into three groups: group 1—instillation of isotonic saline, group 2—ALI treated with saline, group 3—ALI treated with RC-3095 (5 mg/kg, s.c. 3 h after ALI) (n=36). To estimate the degree of alveolar cell injury and the alveolar-capillary membrane compromise BALF total cell count and differential, BALF protein and lactate dehydrogenase (LDH) content were determined. BALF cells were evaluated using a Neubauer chamber stained with Giemsa or Trypan blue exclusion dye. BALF total protein content was determined by the Lowry assay. BALF total LDH content was determined using a spectrophotometer by commercially available kits (Lab-Trade, Brazil).

I.2.3 Macrophage Release of TNF-α, IL-1β and IL-10

Peritoneal macrophages were prepared from freshly isolated peritoneal exudates of Wistar rats (normal rat or rat 4 hrs after CLP). For the isolation of macrophages $2\times10^7$ peritoneal exudate cells in 10 mL of RPMI-1640 medium (Sigma Chemical, St. Louis, Mo.) supplemented with 2% heat-inactivated fetal bovine serum were cultured Petri dishes for 60 mins at 37° C. (ref CCM). Then macrophages were cultured in RPMI-1640 medium supplemented with 10% heat-inactivated fetal bovine serum for further 4 hours. After this period macrophages isolated form normal rat were exposed to LPS (100 ng/ml for 4 h) and then assigned to the bombesin/GRP antagonist RC-3095 (1 μg/mi or 10 μg/ml) or not. After 6 h the medium was recovered to the determination of TNF-α, IL-1β and IL-10. Macrophages isolated from CLP exposed animals were cultured as described above and treated with or without RC-3095 for 6 h. After this period the medium was recovered to the determination of TNF-α, IL-1β and IL-10.

I.3. Results and Discussion

I.3.1 Bombesin/GRP Antagonist Modulation of TNF-α and IL-1β, but not IL-10, Release from Macrophages Primary cultures of rat peritoneal macrophages were stimulated with endotoxin and treated them with the bombesin/GRP antagonist RC-3095. The bombesin/GRP antagonist attenuated LPS-induced TNF-α and IL-1β accumulation in the culture media of macrophages. This effect was more pronounced at 10 µg/ml (Table 1), but was evident at 1 µg/ml (data not shown). The bombesin/GRP antagonist did not interfere with the release of the anti-inflammatory cytokine IL-10 in both doses studied (data not shown). These results were similar when peritoneal macrophages from CLP rats were studied. The release of TNF-α and IL-1β, but not IL-10, by CLP-activated macrophages was attenuated, with a maximum inhibition of 50% at a 10 µg/mi concentration (Table 1). RC-3095 at 1 µg/ml also attenuated TNF-α and IL-1β-released from CLP-activated macrophages (data not shown).

TABLE 1

TNF-α and IL-1β released by peritoneal macrophages isolated form normal rat exposed to LPS (100 ng/ml) or isolated from CLP exposed animals treated or not with RC-3095 (10 µg/ml).

|  | TNF-α | IL-1β |
|---|---|---|
| M-LPS | 1400 ± 102 | 250 ± 19 |
| M-LPS + RC | 540 ± 86* | 102 ± 12* |
| M-CLP | 1983 ± 213 | 287 ± 32 |
| M-CLP + RC | 890 ± 123* | 134 ± 11* |

M-LPS - peritoneal macrophages isolated form normal rat exposed to LPS
M-LPS + RC - as M-LPS treated with RC-3095
M-CLP - peritoneal macrophages isolated from CLP rats
M-CLP + RC - as M-CLP treated with RC-3095
*different from M-LPS or M-CLP, $p < 0.05$ These data demonstrate that the bombesin/GRP antagonist RC-3095 inhibits macrophage release of TNF-α and IL-1β and this could block several processes associated with sepsis progression. Interestingly, RC-3095 does not modulate the release of the anti-inflammatory IL-10, suggesting that the intracellular pathway modulated by bombesin/GRP is selective to pro-inflammatory cytokines.

I.3.2 Bombesin/GRP Antagonist Treatment Improves Survival in Experimental Sepsis To determine whether the treatment by the bombesin/GRP antagonist RC-3095 could attenuate circulating TNF-α and IL-1β levels during sepsis, CLP was performed, a clinically relevant animal model for human sepsis because it causes lethal peritonitis produced by a polymicrobial infection (Ritter et al., *Crit. Care Med.* 32, 342-349 (2004)). The treatment was started 6 h after the induction of sepsis, the time at which rat clear signs of sepsis. This delayed administration of RC-3095 attenuates circulating TNF-α and IL-1β levels 24 h after sepsis induction (Table 2).

As demonstrated to the release of IL-10 from macrophages, RC-3095 did not modulate the circulating IL-10 levels during sepsis (data not shown). This delayed RC-3095 administration significantly improved survival when administered with basic support (FIG. 1). The RC-3095 administration 6 hours after CLP once a day for 1 day did not improved mortality when compared to "basic support" (data not shown), but the protective effect was pronounced in animals receiving RC-3095 once a day for 2 days (FIG. 1). The administration of RC-3095 1 h before or 1 h after CLP without basic support significantly improved survival by approximately 50% (data not shown). These protective effects were probably related to the attenuation of damage in pancreas (as assessed by circulating amylase levels), liver (as assessed by circulating aspartate aminotransferase (AST) and serum glutamate pyruvate transaminase (ALT) levels), and to a less extent to the kidney (as assessed by urea and creatinine circulating levels) (Table 2).

Figure 2:
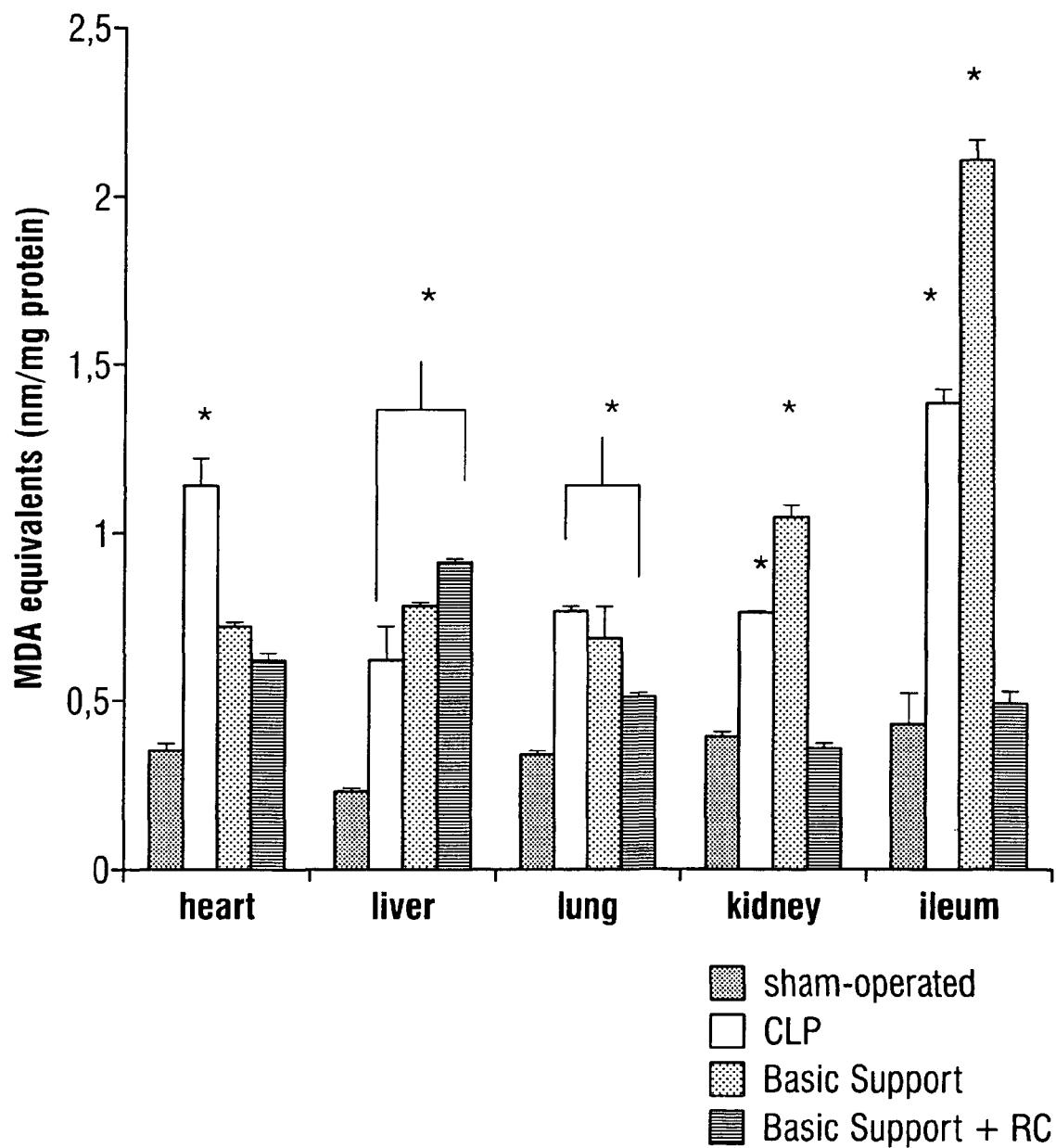
FIG. 2 shows the thiobarbituric acid reactive species content in major organs associated with septic response. Rats were sham-operated or submitted to cecal ligation and puncture (CLP). CLP animals were assigned to receive "basic support", RC-3095 with "basic support", or only saline as described in the Example. 24 hours after CLP the heart, ileum, liver, lung and kidney were removed to the determination of thiobarbituric acid reactive species content as described in the Example. Values are expressed as means±S.D. (n=6 each group).
different from sham-operated, $p<0.05$
different from CLP, $p<0.05$
Figure 3:
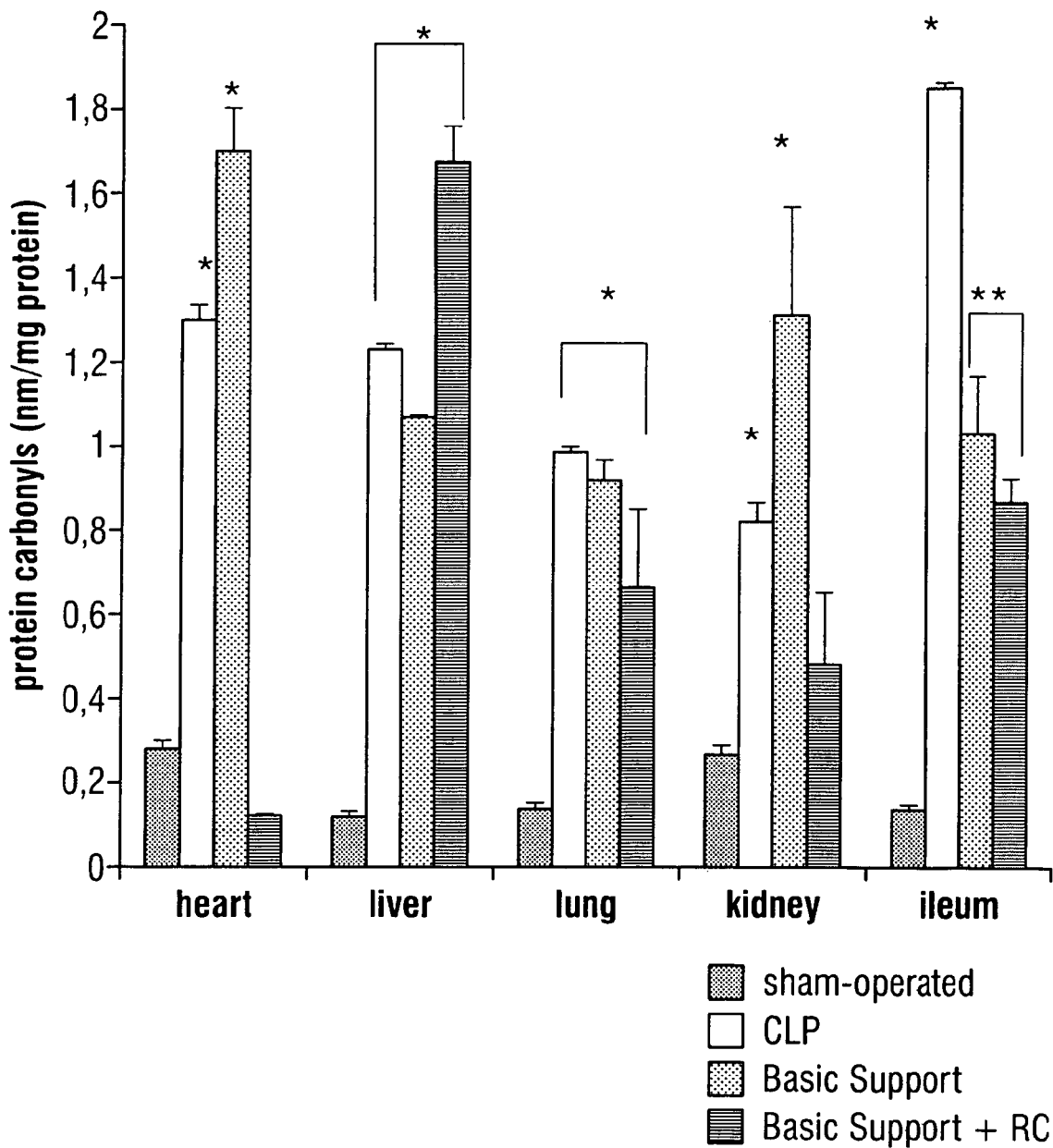
FIG. 3 shows the protein carbonyls content in major organs associated with septic response. Rats were sham-operated or submitted to cecal ligation and puncture (CLP). CLP animals were assigned to receive "basic support", RC-3095 with "basic support", or only saline as described in the Example. 24 hours after CLP the heart, ileum, liver, lung and kidney were removed to the determination of protein carbonyls content as described in the Example. Values are expressed as means±S.D. (n=6 each group).
different from sham-operated, $p<0.05$
different from CLP, $p<0.05$
Figure 4A:
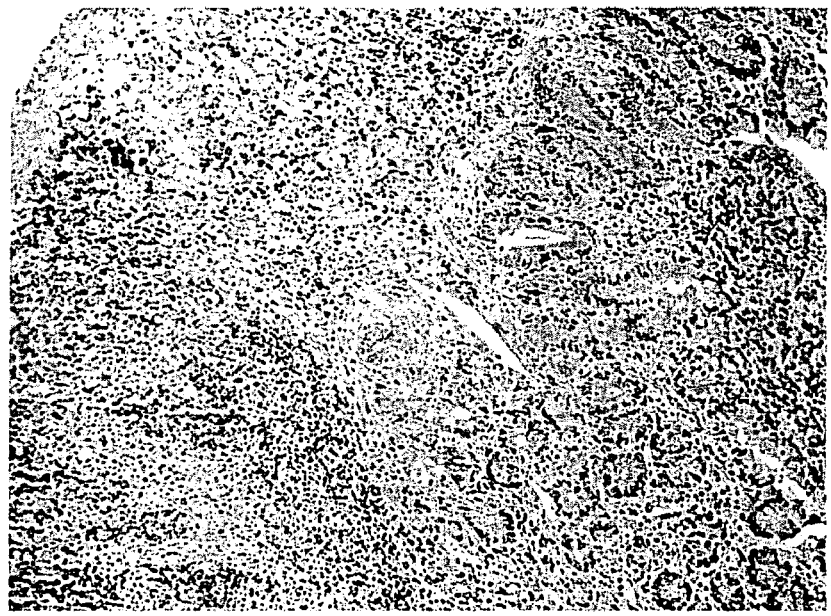
FIG. 4 shows the histopathologic findings 24 h after cecal ligation and puncture (CLP). Rats were submitted to CLP and assigned to receive "basic support" or RC-3095 with "basic support" as described in the Example. 24 hours after CLP the heart (not shown), ileum (A and B), liver (not shown), lung (C and D) and kidney (E and F) were removed for histopathologic analyses as described in the Example. Representative illustrations (n=3). A, C and E rats submitted to CLP that receive "basic support". B, D and F rats submitted to CLP that receive "basic support" plus RC-3095 (Hematoxylin and eosin X 400).
Figure 4B:
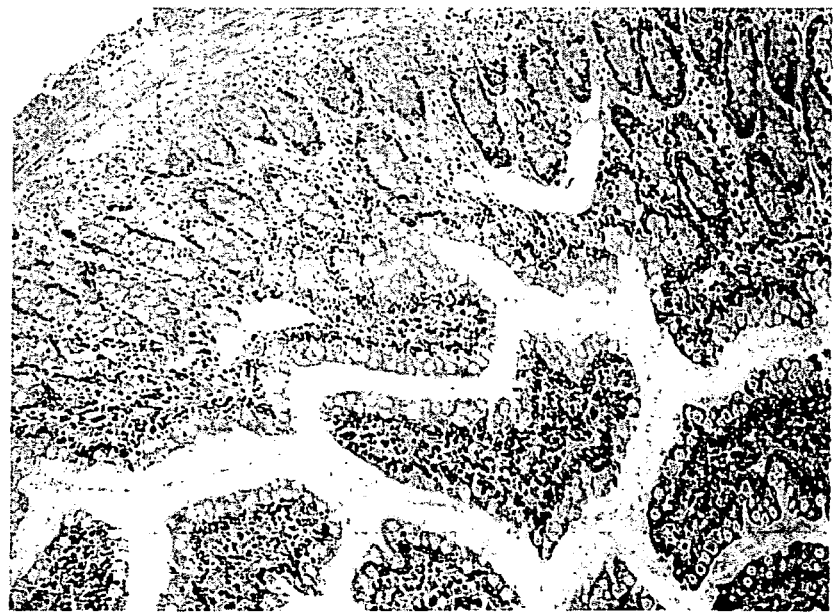
Figure 4C:
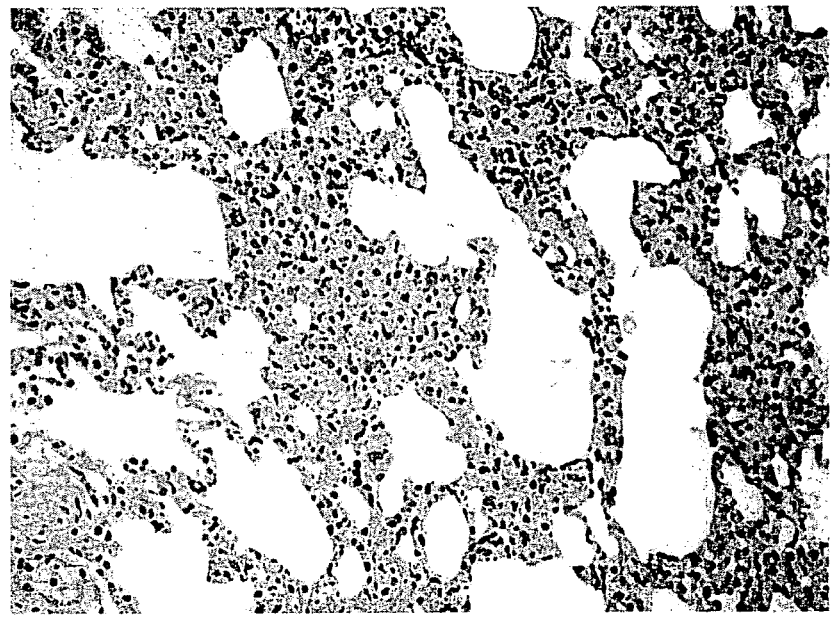
Figure 4D:
Figure 4E:
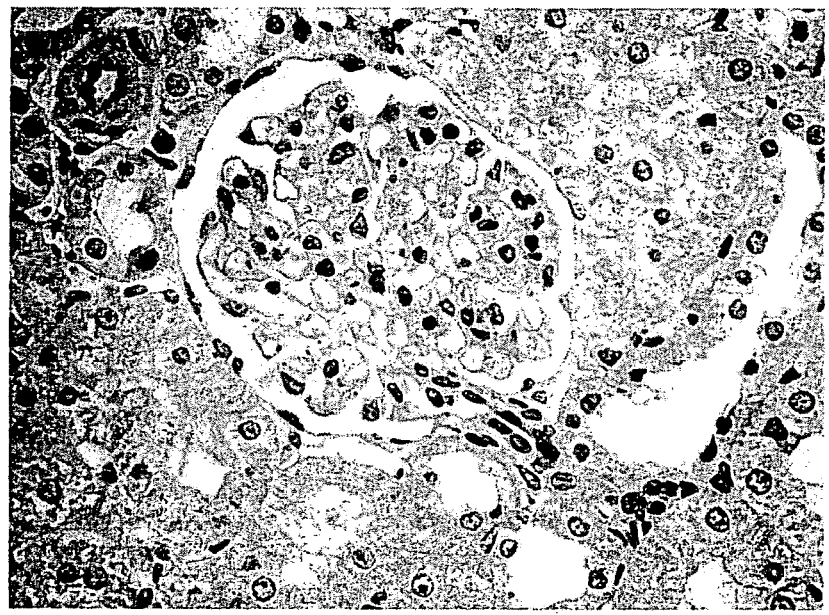
Figure 4F:
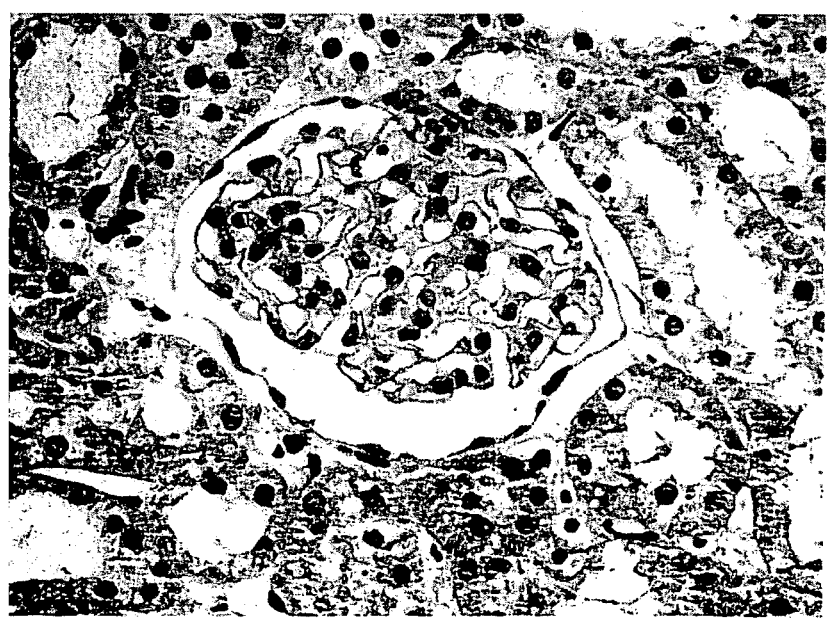

The treatment by the bombesin/GRP antagonist RC-3095 attenuated oxidative damage in several organs associated with the septic response as assessed by TBARS and protein carbonyls levels (FIGS. 2 and 3). This effect was more pronounced in the kidney, ileum and heart (FIGS. 2 and 3). The RC-3095 treatment could attenuate some of the hystopathological alterations observed under optic microscopic observation. The bombesin/GRP antagonist diminished the ileal inflammatory infiltration (FIGS. 4A and 4B), alveolar edema and inflammatory infiltration (FIGS. 4C and 4D) and the mild occurrence of renal tubular necrosis (FIGS. 4E and 4F). The protection against ileal damage was further evidenced by the 3-fold reduction of bacteria counting in mesenteric lymph nodes (data not shown).

TABLE 2

Serum biochemical markers of organ damage and inflammatory response after CLP.

| | CLP | | BS | | RC-3095 | |
| | Time after CLP | | | | | |
| | 12 h | 24 h | 12 h | 24 h | 12 h | 24 h |
|---|---|---|---|---|---|---|
| Urea (mg/dl) | 48 ± 1.3 | 54 ± 2.1 | 47 ± 1.7 | 26 ± 0.6* | 27 ± 0.9* | 27 ± 0.5* |
| Creatinine (mg/dl) | 0.3 ± 0.01 | 0.4 ± 0.03 | 0.4 ± 0.03 | 0.3 ± 0.01 | 0.2 ± 0.01 | 0.2 ± 0.02 |
| AST (UI/l) | 418 ± 23 | 497 ± 31 | 425 ± 26 | 393 ± 32 | 276 ± 19* | 301 ± 21* |
| ALT (UI/l) | 87 ± 7 | 102 ± 12 | 102 ± 10 | 87 ± 9 | 59 ± 7* | 52 ± 10 |
| Amylase (UI/l) | 3136 ± 100 | 2970 ± 99 | 2956 ± 129 | 2863 ± 131 | 2010 ± 102* | 1900 ± 121* |
| TNF-α (pg/ml) | 3400 ± 198 | 2600 ± 175 | 2100 ± 99* | 1200 ± 102* | 1130 ± 92** | 1021 ± 102* |
| IL-1β (pg/ml) | 430 ± 41 | 338 ± 37 | 367 ± 44 | 201 ± 32* | 209 ± 24* | 178 ± 21* |

CLP - septic group (n = 6)
BS - septic group with basic support (n = 6)
RC-3095 - septic group with basic support plus RC-3095 (n = 6)
*different from CLP group, $p < 0.05$
**different from BS group, $p < 0.05$ I.3.2.1 Bombesin/GRP Antagonist Treatment Attenuates Damage in Experimental Acute Lung Injury To determine the effects of the bombesin/GRP antagonist RC-3095 in other animal model of inflammatory disease studies were performed in an experimental model of acute lung injury (ALI) induced by LPS. The RC-3095 treatment after acute lung injury (ALI) induction partially protects lung parenchyma from LPS-induced oxidative damage (FIG. 5). The bombesin/GRP antagonist attenuated the alveolar inflammatory infiltration and alveolar exudation induced by LPS. These findings were supported by the BALF content of inflammatory cells, LDH and protein content (Table 3). RC-3095 administration reduced the BALF total inflammatory cell content (Table 3) and protein exudation (Table 3). In addition, the RC-3095 treatment diminished the BALF LDH content (as an index of alveolar cell injury) (Table 3).

TABLE 3

Cellular and biochemical parameters in the BALF of rats 12 hours after intra-tracheal LPS

| Group | Total cell count ($\times 10^5$) | Total protein (mg/ml) | LDH activity (UI/l) |
|---|---|---|---|
| Control | 51 ± 3.4 | 40 ± 3.2 | 1.2 ± 0.1 |
| LPS | 500 ± 21* | 78 ± 6.5* | 16.2 ± 2.3* |
| LPS + RC | 97 ± 4.6** | 37 ± 2.1 | 8.3 ± 1.2** |

Control - saline instillation (n = 6)
LPS - LPS induced acute lung injury (n = 6)
LPS + RC - LPS induced acute lung injury plus RC-3095 (n = 6)
*different from control, p < 0.05
**different from LPS, p < 0.05

II)

Here, the inventors of the present invention demonstrate the therapeutic potential of the bombesin/GRP antagonist RC-3095 for the treatment or prophylaxis of brain disorders, particularly bipolar disorder by means of a rodent model of mania (amphetamine-induced hyperactivity in rats).

Although there is at present no suitable animal model for bipolar disorder (BD), some simple behavioural models of mania have been proposed. These are based on hyperactivity, which is one of the core symptoms of mania that can be mimicked in animals. Hyperactivity induced by d-amphetamine has been proposed to be a useful model for mania, since the behaviour elicited can be attenuated by lithium or anti-epileptic drugs administration at doses that did not decrease locomotor activity per se. Low doses of amphetamine, such as 0.5-4.0 mg/kg, produce an increase in locomotor activity, while higher doses, such as 5.0-10.0 mg/kg, induce stereotyped behaviour (Einat et al., 2000; Machado-Vieira et al., 2004; Frey et al., 2005). Case reports have suggested that the euphoric effects induced by amphetamine in human beings can be attenuated by lithium administration. In fact, the magnitude of ventral striatal dopamine release induced by amphetamine correlated positively with the hedonic response in human subjects (Strakowski et al., 1998; Anand et al., 2000).

Bombesin (BN) is one of the active peptides purified from amphibian skin. This peptide is also active in mammals and its pharmacological effect extends into various physiological aspects. Receptors for bombesin-like peptide are G-protein-coupled receptors expressed in various brain regions, lung and in the digestive tract (for a recent review, see Moody and Merali, 2004). The evidence that BN-like peptides are also involved in the pathogenesis of several types of human cancer has led to the development of BN/GRP receptor antagonists such as RC-3095 as potential anticancer drugs (Radulovic et al., 1991). Bombesin-like peptides regulate several aspects of CNS function, including feeding, satiety, aversion, reward, anxiety, as well as learning and memory processes (Roesler et al., 2004).

By the established rat model of acute mania/bipolar disorder it is demonstrated that RC-3095 may be an alternative therapeutic strategy for the treatment or prophylaxis of brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder.

II.1 Material and Methods

Animals. A total of 120 male Wistar rats (age, 2.5-3 months; weight, 220-340 g) from an inhouse breeding colony were used. They were housed in plastic cages, 5 to a cage, with water and food freely available, under a 12-h light/dark cycle (lights on at 7:00 h). All experimental procedures were performed in accordance with the NIH Guide for the Care and Use of Laboratory Animals and the Brazilian Society for Neuroscience and Behavior (SBNeC) recommendations for animal care.

Drugs and pharmacological procedures. d-amphetamine (AMPH, 2.0 mg/kg) and RC-3095 (a gift from Dr. J. Engel, Zentaris GmbH, Germany) were dissolved in saline (SAL, 0.9% NaCl). All solutions were prepared immediately prior to administration. Animals were given a 10 ml/kg intraperitoneal (i.p.) injection of SAL or RC-3095 (0.1, 1.0 or 10.0 mg/kg) followed by an i.p. injection of SAL or AMPH (1.0 mg/kg) 30 min later. Thus, the resulting experimental groups were: SAL/SAL; SAL/AMPH, RC-3095 0.1 mg/kg/AMPH, RC-3095 1.0 mg/kg/AMPH, RC-3095 10.0 mg/kg/AMPH, RC 3095 0.1 mg/kg/SAL; RC-3095 1.0 mg/kg/SAL; and RC-3095 10.0 mg/kg/SAL.

Hyperactivity test. Animals were placed in a 40×60 cm open-field surrounded by 50-cm high walls made of brown plywood with a frontal glass wall. The floor of the open field was divided into 12 equal rectangles by black lines. Animals were gently placed on the left rear quadrant, and left to explore the arena for 5 min. Crossings of the black lines and rearings performed were counted. The number of crossings and rearings was taken as a measure of hyperactivity (Frey et al., 2005).

Statistical analysis. All data are presented as mean±S.E.M. Differences among experimental groups were determined by ANOVA. Multiple comparisons were performed by a Tukey test. In all experiments, p values less than 0.05 were considered to indicate statistical significance.

II.2 Results and Discussion

AMPH increased locomotion and rearing behavior in rats pretreated with SAL+RC-3095 prevented AMPH-related hyperactivity at all doses used (FIG. 6). Administration of RC-3095 did not alter other behavioral measures, indicating that the effects of RC-3095 in AMPH-treated rats were not associated with sedation.

The present results indicate that systemic administration of RC-3095 displays anti-manic effects. These effects were shown in an animal model of acute mania induced by amphetamine. Despite of the well-recognized limitations of animal models of bipolar disorder in terms of face validity (Frey et al., 2005: Machado-Vieira et al., 2004; Einat et al., 2000), it is well known that AMPH induces manic symptoms in patients with BD (Anand et al., 2000) as well as in healthy volunteers (Strakowski and Sax., 1998).

Even though the precise pathophysiology of BD is far from being fully elucidated, recent studies have demonstrated that BD is associated with changes in intracellular signaling pathways that modulate neuronal plasticity and survival. Cellular signaling pathways associated with the pathogenesis of BD include the protein kinase C (PKC) and the mitogen-activated protein kinase (MAPK) pathways (Manji and Lenox, 2000; Manji and Chen, 2002), which are also importantly regulated by BN/GRP receptors (Hellmich et al., 1999; Moody and Merali, 2004). A number of treatments for acute mania, such as lithium, valproate and atypical antipsychotics are also used to prevent new episodes of the bipolar disorder.

In summary, the results provide preclinical evidence that BN/GPR receptor antagonists such as RC-3095 may display anti-manic and mood stabilizing properties and could be used in the treatment or prophylaxis of BD.

Anand, A., Verhoeff, P., Seneca, N., Zoghbi, S. S., Seibyl, J. P., Charney, D. S., Innis, R. B., 2000. Brain SPECT imaging of amphetamine-induced dopamine release in euthymic bipolar disorder patients. American Journal of Psychiatry 157(7), 1108-1114.

Einat, H., Kofman, O., Belmaker, R. H. 2000. Animal models of bipolar disorder: from a single episode to progressive cycling models. In: Myslobodsky, M., Weiner, I. (Eds.), Contemporary issues in modeling psychopharmacology. Boston: Kluwer Academic Publishers, pp. 165-180.

Frey, B. N., Martins, M. R., Petronilho, F. C., Dal-Pizzol, F., Quevedo, J., Kapczinski, F., 2005. Increased oxidative stress after repeated amphetamine exposure: possible relevance as an animal model of acute mania. Bipolar Disorders (in press).

Hellmich, M. R., Ives, K. L., Udupi, V., Soloff, M. S., Greeley, G. H. Jr., 1999. Christensen B N, Townsend C M Jr. Multiple protein kinase pathways are involved in gastrin-releasing peptide receptor-regulated secretion. Journal of Biological Chemistry 274, 23901-23909.

Machado-Vieira, R., Kapczinski, F., Soares, J. C., 2004. Perspectives for the development of animal models of bipolar disorder. Progress in Neuro-Psychopharmacology and Biological Psychiatry 28, 209-224.

Manji, H. K., Chen, G., 2002. PKC, MAP kinases and the bcl-2 family of proteins as long-term targets for mood stabilizers. Molecular Psychiatry 7(Suppl 1), S46-56.

Manji, H. K., Lenox, R. H., 2000. Signaling: cellular insights into the pathophysiology of bipolar disorder. Biological Psychiatry 48, 518-530.

Moody, T. W., Merali, Z., 2004. Bombesin-like peptides and associated receptors within the brain: distribution and behavioral implications. Peptides 25, 511-520.

Radulovic, S., Cai, R. Z., Serfozo, P., Groot, K., Redding, T. W., Pinski, J., Schally, A. V., 1991. Biological effects and receptor binding affinities of new pseudononapeptide bombesin/GRP receptor antagonists with N-terminal D-Trp or D-Tpi. International Journal of Peptide and Protein Research 38, 593-600.

Roesler, R., Henriques, J. A. P., Schwartsmann, G., 2004. Neuropeptides and anxiety disorders: bombesin receptors as novel therapeutic targets. Trends in Pharmacological Sciences 25, 241-242.

Strakowski, S. M., Sax, K. W., 1998. Progressive behavioral response to repeated d-amphetamine challenge: further evidence for sensitization in humans. Biological Psychiatry 44, 1171-1177.

The invention method and compositions are preferably used by subjects (patients) desirous of the benefits noted herein, subjects "in need of" these benefits. Such subjects are typically suffering from, e.g., sepsis, acute lung injury and rheumatoid arthritis, brain disorders, preferably bipolar disorder, and in particular the different forms and/or subforms of bipolar disorder, such as mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder and/or rapid-cycling bipolar disorder, such as by self diagnosis or medical diagnosis, or are at recognized and appreciated risk of developing such conditions and who use the invention methods and compositions to combat these effects. In this regard, the invention process can be viewed as one for delaying the onset of the appearance of, and/or for reducing signs of, these conditions and disorders.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference.

Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A method of treating a patient having septic shock comprising: administering to said patient RC-3095 (SEQ ID NO: 1), or a pharmaceutically acceptable salt thereof, in an amount sufficient to treat the septic shock.

2. A method of treating a patient having acute lung injury comprising administering to said patient RC-3095 (SEQ ID NO: 1), or a pharmaceutically acceptable salt thereof, in an amount sufficient to treat the acute lung injury.

* * * * *